United States Patent
Lynch et al.

(10) Patent No.: US 9,254,370 B2
(45) Date of Patent: Feb. 9, 2016

(54) FRAME AND VENT ASSEMBLY FOR MASK ASSEMBLY

(75) Inventors: Susan Robyn Lynch, Bella Vista (AU); Philip Thomas Stallard, Denistone East (AU); Scott Alexander Howard, Harbord (AU); Joshua Adam Gudiksen, Mortdale (AU); Murray William Lee, Quakers Hill (AU); Matthew Eves, Carlingford (AU); Melanie Lucia Cariola, Epping (AU)

(73) Assignee: ResMed Limited, Bella Vista (AU)

( * ) Notice: Subject to any disclaimer, the term of this patent is extended or adjusted under 35 U.S.C. 154(b) by 612 days.

(21) Appl. No.: 12/312,308

(22) PCT Filed: Nov. 14, 2007

(86) PCT No.: PCT/AU2007/001749
§ 371 (c)(1),
(2), (4) Date: May 5, 2009

(87) PCT Pub. No.: WO2008/058330
PCT Pub. Date: May 22, 2008

(65) Prior Publication Data
US 2010/0051034 A1 Mar. 4, 2010

Related U.S. Application Data

(60) Provisional application No. 60/858,700, filed on Nov. 14, 2006.

(51) Int. Cl.
| | |
|---|---|
| *A61M 16/00* | (2006.01) |
| *A61M 16/06* | (2006.01) |
| *A62B 18/02* | (2006.01) |
| *A62B 18/08* | (2006.01) |

(52) U.S. Cl.
CPC ........... *A61M 16/06* (2013.01); *A61M 16/0633* (2014.02); *A61M 2205/42* (2013.01)

(58) Field of Classification Search
CPC .......................... A61M 16/06; A61M 16/0633
USPC ............. 128/206.21, 206.28, 206.12, 203.29, 128/205.25, 207.13
See application file for complete search history.

(56) References Cited

U.S. PATENT DOCUMENTS

| | | | |
|---|---|---|---|
| 2,603,215 | A | 7/1952 | Arnow |
| 2,738,788 | A | 3/1956 | Matheson et al. |
| 2,742,821 | A | 4/1956 | Sweetman |

(Continued)

FOREIGN PATENT DOCUMENTS

| | | |
|---|---|---|
| GB | 880824 | 10/1961 |
| WO | WO 98/34665 | 8/1998 |

(Continued)

OTHER PUBLICATIONS

U.S. Appl. No. 29/258,084, filed Apr. 2006, Judson et al.

(Continued)

*Primary Examiner* — Loan H Thanh
*Assistant Examiner* — Sundhara Ganesan
(74) *Attorney, Agent, or Firm* — Nixon & Vanderhye, P.C.

(57) ABSTRACT

A nasal or full-face mask frame includes a main body and a vent assembly provided to the main body. The vent assembly includes a plurality of holes arranged in at least one column. The holes are positioned on a relatively flat and/or non-recessed portion of the main body.

51 Claims, 27 Drawing Sheets

(56) References Cited

U.S. PATENT DOCUMENTS

| | | | |
|---|---|---|---|
| 3,118,445 | A | 1/1964 | Marius |
| 3,228,610 | A | 1/1966 | Quaas et al. |
| 3,425,600 | A | 2/1969 | Abplanalp |
| 3,633,575 | A | 1/1972 | Brumfield |
| 3,850,171 | A * | 11/1974 | Ball et al. ............... 128/204.25 |
| 4,090,510 | A | 5/1978 | Segersten |
| 4,161,516 | A | 7/1979 | Bell |
| 4,328,797 | A * | 5/1982 | Rollins et al. ............ 128/202.27 |
| 4,347,633 | A | 9/1982 | Gammons et al. |
| 4,424,106 | A | 1/1984 | Rossoshinsky et al. |
| 4,782,832 | A | 11/1988 | Trimble et al. |
| 4,856,508 | A | 8/1989 | Tayebi |
| 4,989,596 | A * | 2/1991 | Macris et al. ............ 128/201.28 |
| 5,042,478 | A | 8/1991 | Kopala et al. |
| 5,195,773 | A | 3/1993 | Sawada et al. |
| 5,324,295 | A | 6/1994 | Shapiro |
| 5,431,158 | A * | 7/1995 | Tirotta .................... 128/206.21 |
| 5,533,506 | A | 7/1996 | Wood |
| 5,656,523 | A | 8/1997 | Wilhoit |
| 5,683,293 | A | 11/1997 | Mohammed |
| 5,687,746 | A | 11/1997 | Rose et al. |
| 5,709,204 | A * | 1/1998 | Lester ..................... 128/205.25 |
| 5,724,965 | A | 3/1998 | Handke et al. |
| 5,740,649 | A | 4/1998 | Fuchs et al. |
| 5,962,349 | A | 10/1999 | Mizukami et al. |
| 6,012,455 | A | 1/2000 | Goldstein |
| 6,017,315 | A | 1/2000 | Starr et al. |
| 6,044,844 | A | 4/2000 | Kwok et al. |
| 6,074,446 | A | 6/2000 | Fujino |
| 6,077,152 | A | 6/2000 | Warehime |
| 6,082,356 | A | 7/2000 | Stradella |
| 6,210,806 | B1 | 4/2001 | Hidaka et al. |
| 6,241,247 | B1 | 6/2001 | Sternberg et al. |
| 6,336,455 | B1 | 1/2002 | Howlett |
| 6,378,518 | B1 | 4/2002 | Miekka et al. |
| 6,401,716 | B1 * | 6/2002 | Sword et al. ............ 128/206.21 |
| 6,431,172 | B1 | 8/2002 | Bordewick |
| 6,561,190 | B1 | 5/2003 | Kwok |
| 6,561,191 | B1 | 5/2003 | Kwok |
| 6,581,594 | B1 | 6/2003 | Drew et al. |
| 6,638,588 | B1 | 10/2003 | Bowen et al. |
| 6,691,707 | B1 | 2/2004 | Gunaratnam et al. |
| 6,851,425 | B2 * | 2/2005 | Jaffre et al. ............ 128/204.18 |
| 7,207,335 | B2 | 4/2007 | Kwok et al. |
| 7,686,800 | B2 | 3/2010 | Savage et al. |
| 7,827,990 | B1 | 11/2010 | Melidis et al. |
| 7,836,884 | B2 * | 11/2010 | Wright .................... 128/203.16 |
| 7,845,354 | B2 | 12/2010 | Kwok et al. |
| 7,934,501 | B2 * | 5/2011 | Fu et al. .................. 128/206.21 |
| 7,942,150 | B2 * | 5/2011 | Guney et al. ............ 128/207.14 |
| 8,042,539 | B2 * | 10/2011 | Chandran et al. ....... 128/206.28 |
| 8,122,886 | B2 | 2/2012 | Kwok et al. |
| 8,261,746 | B2 * | 9/2012 | Lynch et al. ............ 128/206.24 |
| 8,297,283 | B2 * | 10/2012 | Hitchcock et al. ...... 128/206.24 |
| 8,397,728 | B2 * | 3/2013 | D'Souza et al. ......... 128/206.24 |
| 2001/0029948 | A1 | 10/2001 | Ingle et al. |
| 2002/0172566 | A1 | 11/2002 | Issler |
| 2003/0005931 | A1 | 1/2003 | Jaffre et al. |
| 2003/0005935 | A1 * | 1/2003 | Kwok et al. ............ 128/206.21 |
| 2003/0075180 | A1 * | 4/2003 | Raje et al. ............... 128/206.24 |
| 2003/0079751 | A1 | 5/2003 | Kwok |
| 2004/0022820 | A1 * | 2/2004 | Anderson ..................... 424/401 |
| 2004/0177850 | A1 | 9/2004 | Gradon et al. |
| 2005/0076913 | A1 * | 4/2005 | Ho et al. ................. 128/206.27 |
| 2005/0092326 | A1 * | 5/2005 | Drew et al. .............. 128/206.21 |
| 2005/0126573 | A1 * | 6/2005 | Jaffre et al. ............. 128/207.12 |
| 2005/0241644 | A1 * | 11/2005 | Gunaratnam et al. ... 128/207.18 |
| 2006/0042629 | A1 * | 3/2006 | Geist ....................... 128/206.24 |
| 2006/0118119 | A1 | 6/2006 | Berthon-Jones et al. 128/207.11 |
| 2006/0174887 | A1 * | 8/2006 | Chandran et al. ....... 128/206.11 |
| 2006/0196509 | A1 * | 9/2006 | Drew et al. .............. 128/206.21 |
| 2006/0201514 | A1 * | 9/2006 | Jones et al. .............. 128/206.21 |
| 2006/0254593 | A1 * | 11/2006 | Chang ..................... 128/206.24 |
| 2006/0266361 | A1 * | 11/2006 | Hernandez ............... 128/206.11 |
| 2007/0044804 | A1 * | 3/2007 | Matula et al. ........... 128/206.21 |
| 2007/0062536 | A1 * | 3/2007 | McAuley et al. ........ 128/206.21 |
| 2007/0095350 | A1 | 5/2007 | Darkin et al. |
| 2007/0175480 | A1 * | 8/2007 | Gradon et al. ........... 128/207.11 |
| 2007/0221226 | A1 * | 9/2007 | Hansen et al. ........... 128/206.21 |
| 2009/0139526 | A1 | 6/2009 | Melidis et al. |
| 2009/0151729 | A1 | 6/2009 | Judson et al. |
| 2009/0277452 | A1 * | 11/2009 | Lubke et al. ............. 128/206.21 |
| 2010/0051034 | A1 | 3/2010 | Howard et al. |
| 2010/0282265 | A1 | 11/2010 | Melidis et al. |
| 2011/0180071 | A1 | 7/2011 | Veliss et al. |
| 2011/0277771 | A1 | 11/2011 | Kwok et al. |

FOREIGN PATENT DOCUMENTS

| | | |
|---|---|---|
| WO | WO 00/13751 | 3/2000 |
| WO | WO 01/62326 A1 | 8/2001 |
| WO | WO 02/066105 | 8/2002 |
| WO | PCT/AU2004/000207 | 2/2004 |
| WO | WO 2004/030736 A1 | 4/2004 |
| WO | WO/2004/073778 | 9/2004 |
| WO | WO 2005/021075 A1 | 3/2005 |
| WO | WO 2005/079726 | 9/2005 |
| WO | PCT/AU2006/000031 | 1/2006 |
| WO | PCT/AU2006/000035 | 1/2006 |
| WO | PCT/AU2006/000037 | 1/2006 |
| WO | WO 2006/069415 | 7/2006 |
| WO | WO 2006/074516 | 7/2006 |
| WO | PCT/AU2006/001507 | 10/2006 |
| WO | WO 2007/053878 | 5/2007 |

OTHER PUBLICATIONS

U.S. Appl. No. 60/795,615, filed Apr. 2006, Smart et al.
International Search Report for PCT/AU2007/001749, dated Jan. 10, 2008.
U.S. Appl. No. 60/734,282, filed Nov. 2005, Judson et al.
U.S. Appl. No. 60/758,200, filed Jan. 2006, Judson et al.
U.S. Appl. No. 60/795,615, filed Apr. 2006, Judson et al.
U.S. Appl. No. 60/819,626, filed Jul. 2006, Judson et al.
U.S. Appl. No. 60/838,442, filed Aug. 2006, Judson et al.
U.S. Appl. No. 11/101,657, filed Apr. 2005, Gunaratnam et al.
U.S. Appl. No. 10/781,929, filed Feb. 2004, Gunaratnam et al.
U.S. Appl. No. 60/795,562, filed Apr. 20006, Scheiner et al.
Examination Report issued in related New Zealand Application No. 590211, Jan. 11, 2011.
International Search Report for PCT/AU2006/001507, dated Jan. 9, 2007.
Examination Report issued in related New Zealand Application No. 567374, Jan. 11, 2011.
Office Action mailed Feb. 2, 2015 in U.S. Appl. No. 12/084,373 (10 pages).
Proceeding Correspondence mailed Oct. 29, 2012 in New Zealand Application No. 590211 (3 pages).
Deadline for Counterstatement mailed Mar. 25, 2013 in New Zealand Application No. 590211 (8 pages).
Office Action mailed Jun. 20, 2014 in U.S. Appl. No. 12/084,373 (41 pages).
Amended Notice of Opposition to Grant of Patent in corresponding New Zealand Patent Application No. 611284 dated Jun. 24, 2015.
Statement of Case in corresponding New Zealand Patent Application No. 611284 dated Jun. 24, 2015.
Sep. 3, 2015 Decision of Assistant Commissioner issued in corresponding New Zealand Application No. 590211.
Aug. 28, 2015 Opponent's Letter to the Applicant in corresponding New Zealand Application No. 611284.
Extension of Time Granted mailed Apr. 29, 2015 in New Zealand Application No. 611284 (1 pg.), with Application Under Regulation 168 for Extension of Time (1 pg.) and Notice of Opposition to Grant of Patent (Section 21) (2 pgs.), filed Apr. 24, 2015.
Sep. 24, 2015 Office Action issued in U.S. Appl. No. 12/084,373 including form PTO-892 listing U.S. Pat. No. 6,418,929.

* cited by examiner

FRAME AND VENT ASSEMBLY FOR MASK ASSEMBLY

CROSS-REFERENCE TO APPLICATIONS

This application is the U.S. national phase of International Application No. PCT/AU2007/001749, filed Nov. 14, 2007, which designated the U.S. and claims the benefit of U.S. Provisional Application No. 60/858,700, filed Nov. 14, 2006, each of which is incorporated herein by reference in its entirety.

FIELD OF THE INVENTION

The present invention relates to a frame and vent assembly for a mask assembly used for Non-invasive Positive Pressure Ventilation (NPPV) and for continuous positive airway pressure (CPAP) therapy of sleep disordered breathing (SDB) conditions such as obstructive sleep apnea (OSA).

BACKGROUND OF THE INVENTION

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human or other mammalian patient via a conduit and a mask. Typically, the mask fits over the mouth and/or nose of the patient. Pressurized air flows to the mask and to the airways of the patient via the nose and/or mouth. As the patient exhales, carbon dioxide gas may collect in the mask. A washout vent in the mask or conduit discharges the exhaled gas from the mask to atmosphere.

The washout vent is normally located in the mask or near the mask in the gas delivery conduit coupled to the mask. The washout of gas through the vent to the atmosphere removes exhaled gases to prevent carbon dioxide build-up, and hence "rebreathing", which represent a health risk to the mask wearer. Adequate gas washout is achieved by selecting a vent size and configuration that allows a minimum safe washout flow at a low operating CPAP pressure, which typically can be as low as 4 cm $H_2O$ for adults and 2 cm $H_2O$ for children.

Noise is a significant issue in CPAP treatment for the patient and/or the patient's bed partner. Excessive noise can lead to patients being non-compliant with the CPAP therapy. One source of noise is the exhaust through the vent in the mask or conduit. The flow of gas through the vent creates noise as it exits to and interacts with the atmosphere. Noise can adversely affect patient and bed-partner comfort, depending on both the magnitude and character of the noise. Further, bi-level gas delivery regimes tend to generate more noise than do constant level gas delivery regimes. This is thought to be due to the extra turbulence created by the gas accelerating and decelerating as it cycles between relatively low and relatively high pressures in the bi-level gas delivery systems.

There is a long felt and continuing need to reduce the noise associated with the washout or venting of exhaled gases. Reducing the noise of gas being exhausted from a mask or conduit can significantly improve the user friendliness of the CPAP treatment.

SUMMARY OF THE INVENTION

One aspect of the invention relates to a nasal or full-face mask frame including a main body and a vent assembly provided to the main body. The vent assembly includes a plurality of holes arranged in at least one column. The holes are positioned on a relatively flat and/or non-recessed portion of the main body.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 to 2-7 are various views of an extra-small size frame for a full facial mask assembly according to an embodiment of the present invention;

FIG. 2-8 is a cross-sectional view of a frame according to an embodiment of the present invention;

FIG. 2-9 is an enlarged cross-section view of a vent hole according to an embodiment of the present invention;

FIG. 2-10 is an enlarged plan view of a relatively flat portion of a frame and vent assembly according to an embodiment of the present invention;

FIGS. 3-1 to 3-7 are various views of a small size frame for a full facial mask assembly according to an embodiment of the present invention;

FIGS. 4-1 to 4-7 are various views of a medium size frame for a full facial mask assembly according to an embodiment of the present invention; and FIGS. 5-1 to 5-7 are various views of a large size frame for a full facial mask assembly according to an embodiment of the present invention.

DETAILED DESCRIPTION OF ILLUSTRATED EMBODIMENTS

The following includes descriptions of several illustrated embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

Mask Assembly

Figure 1:
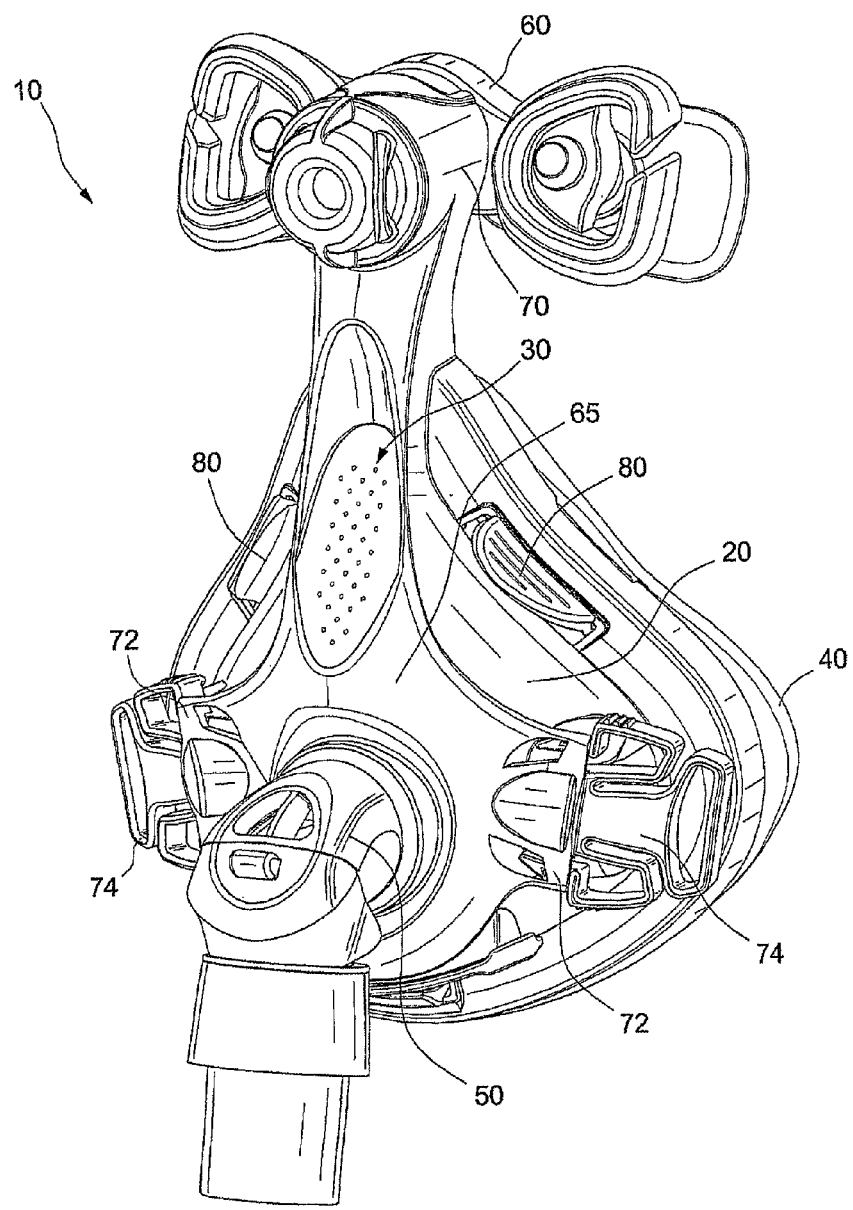
FIG. 1 is a front perspective view of a full facial mask assembly according to an embodiment of the present invention.
Figures 1, 2:
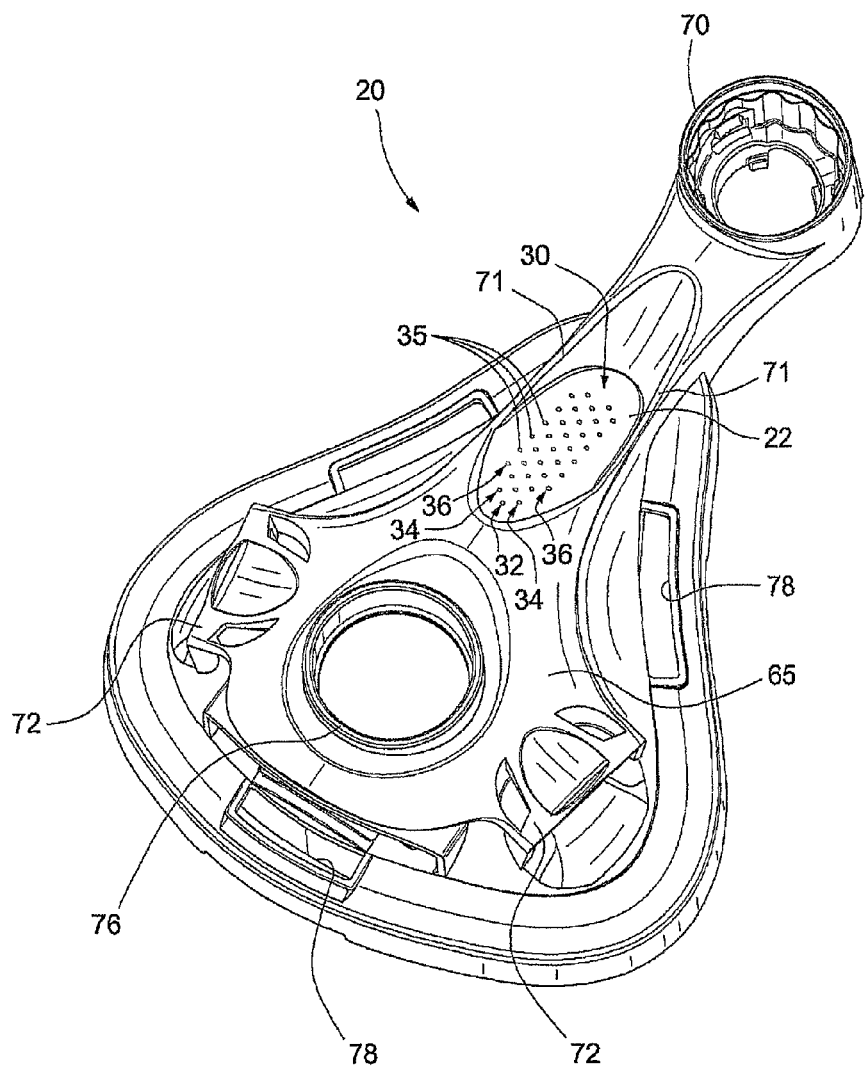
Figure 2:
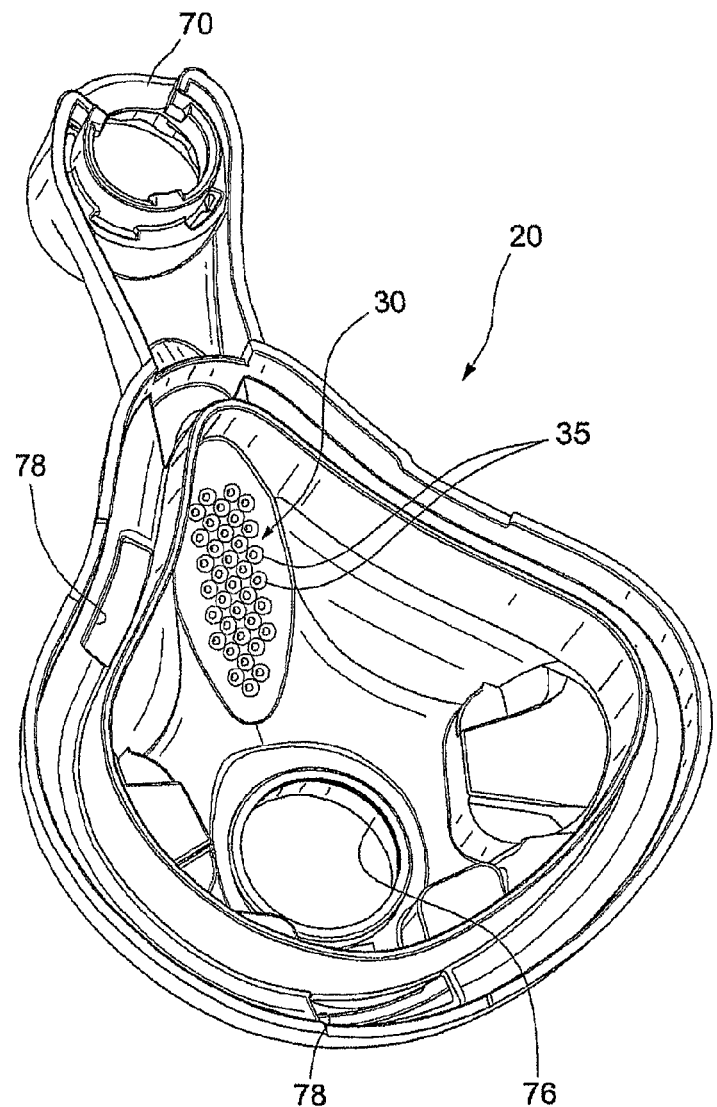
Figures 2, 3:
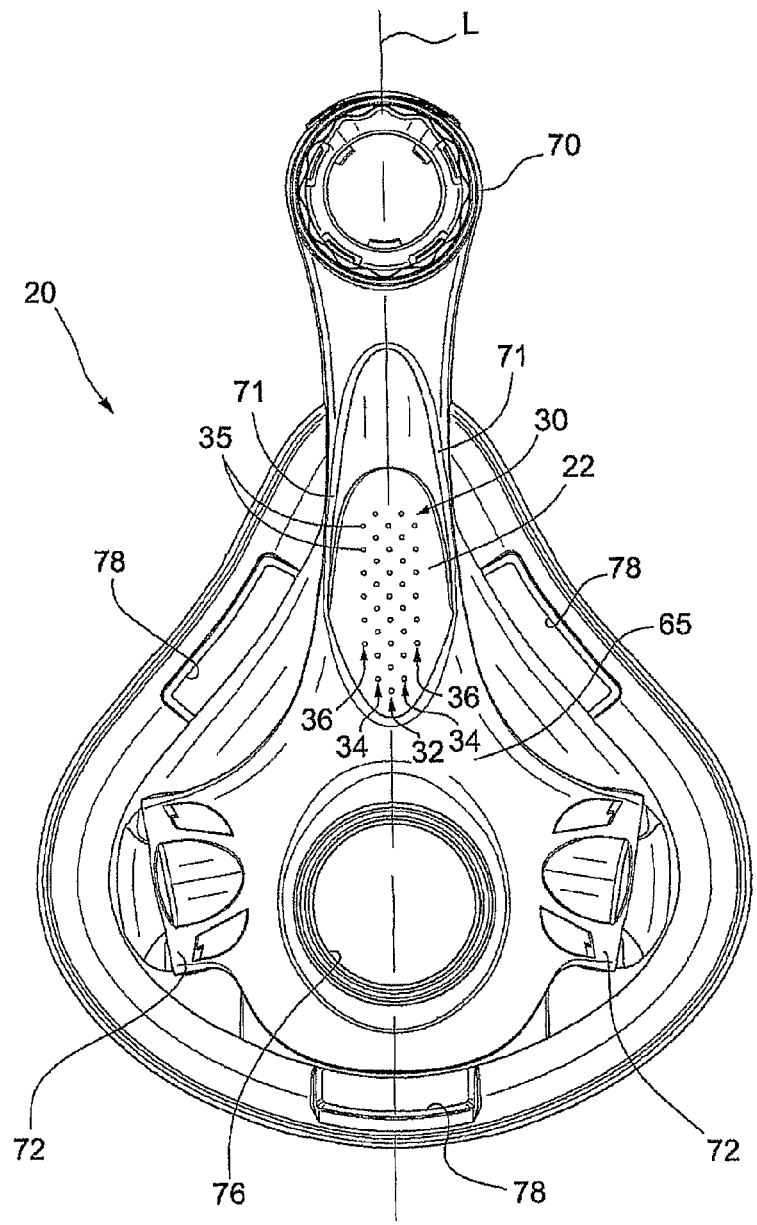
Figures 2, 3, 4:
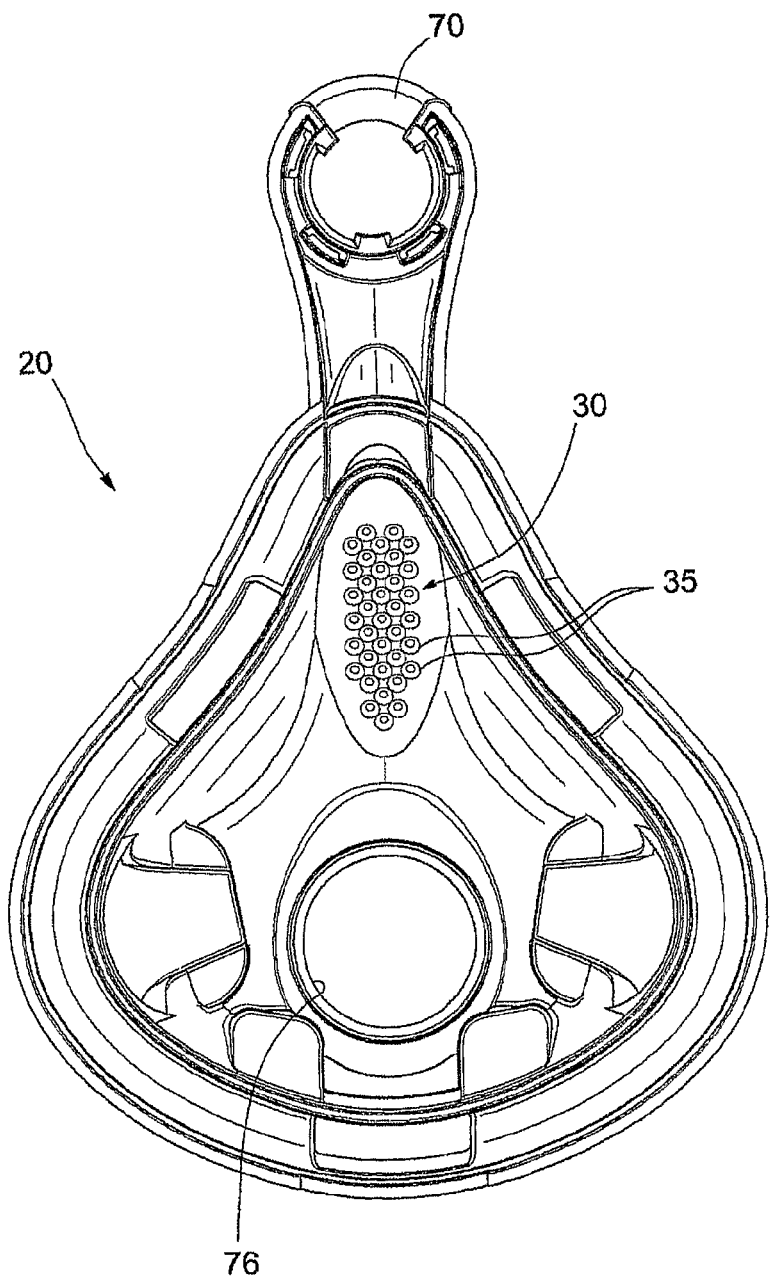
Figures 2, 3, 4, 5:
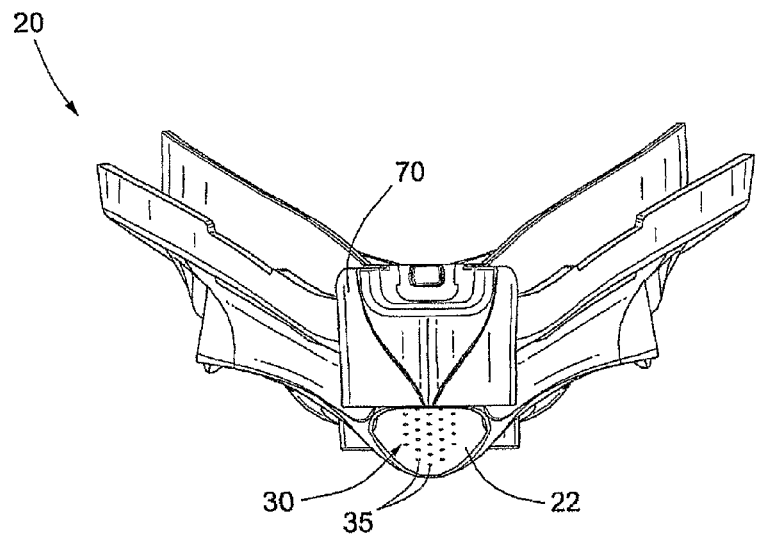
Figures 2, 3, 4, 5, 6:
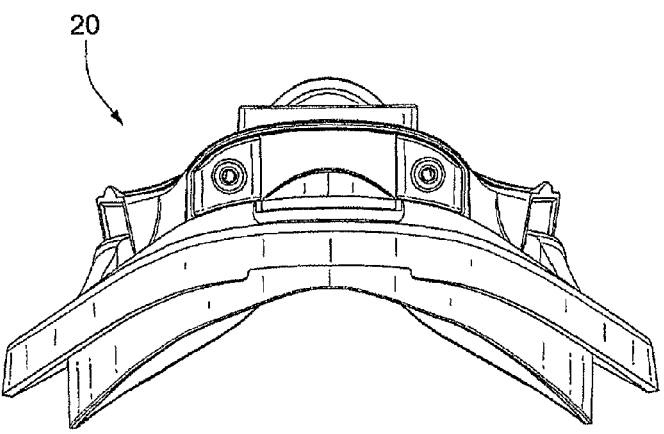
Figures 2, 3, 4, 5, 6, 7:
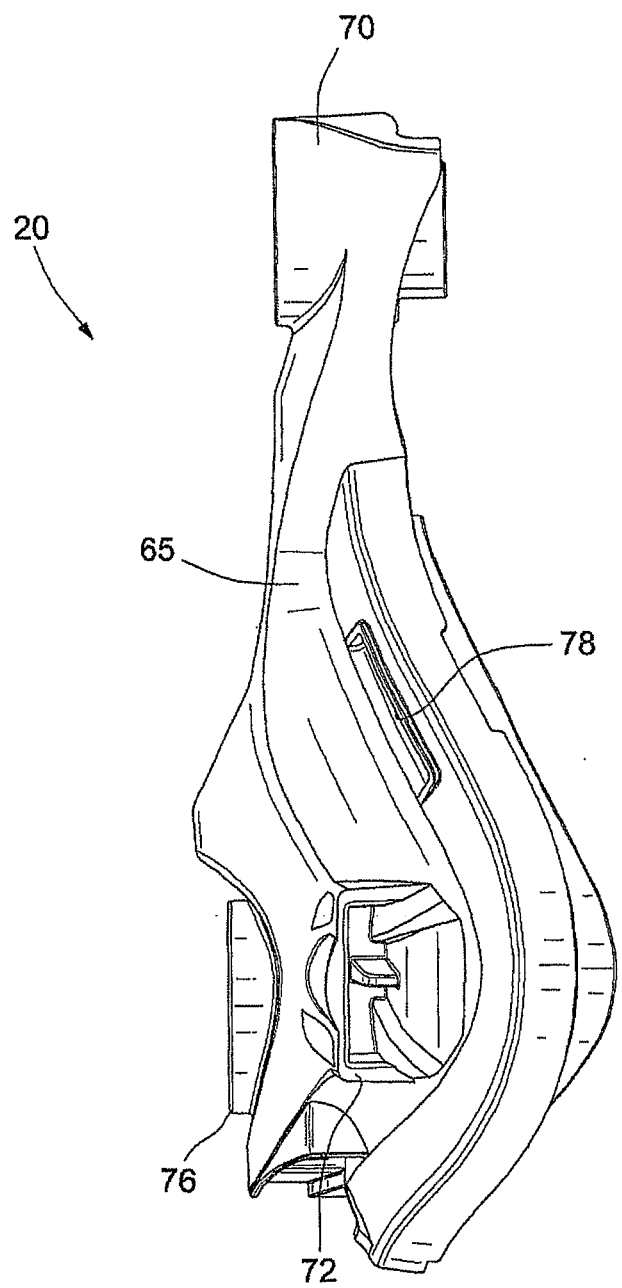
Figures 2, 3, 4, 5, 6, 7, 8:
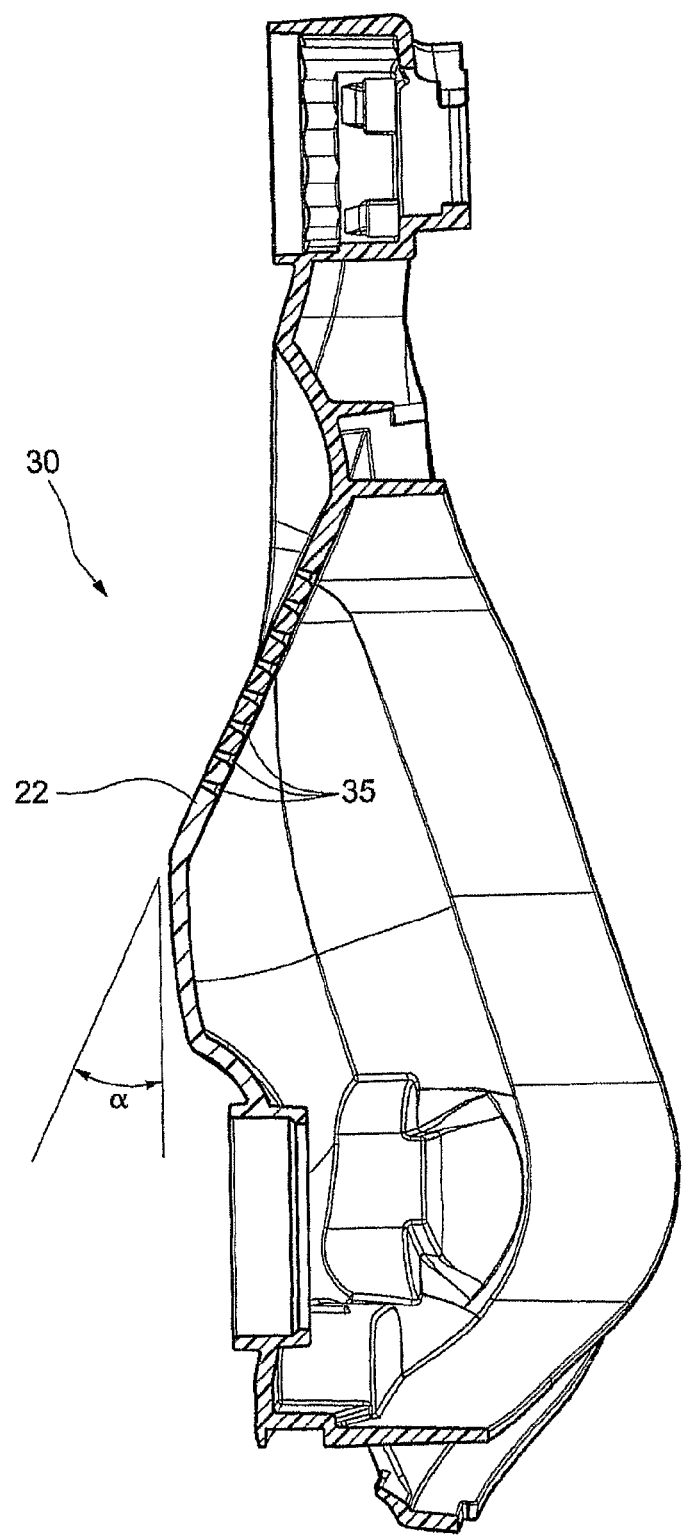
Figures 2, 3, 4, 5, 6, 7, 8, 9:
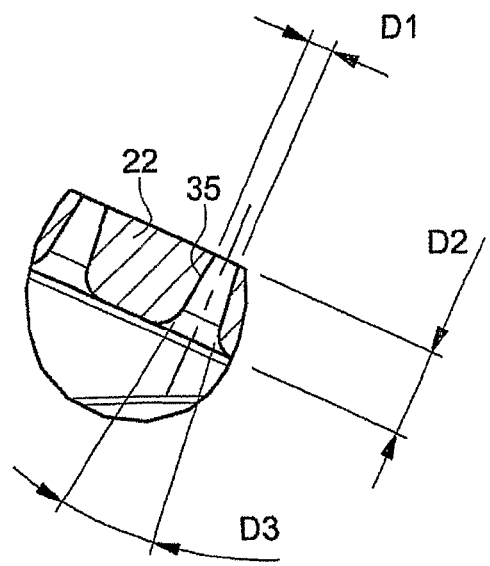
Figures 2, 3, 4, 5, 6, 7, 8, 9, 10:
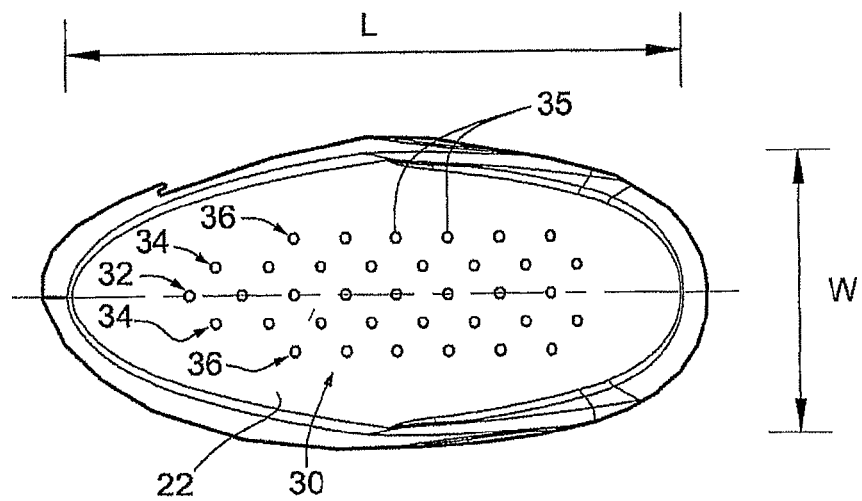
Figures 1, 3:
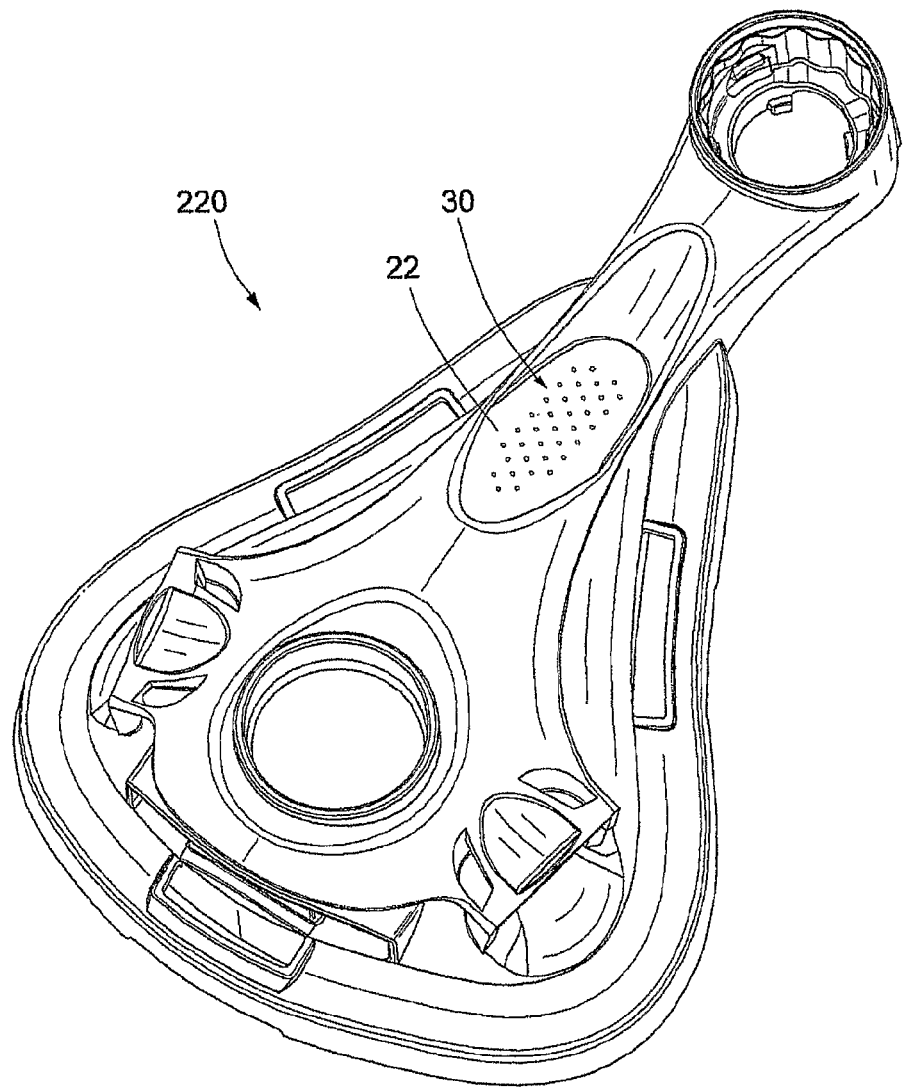
Figures 2, 3:
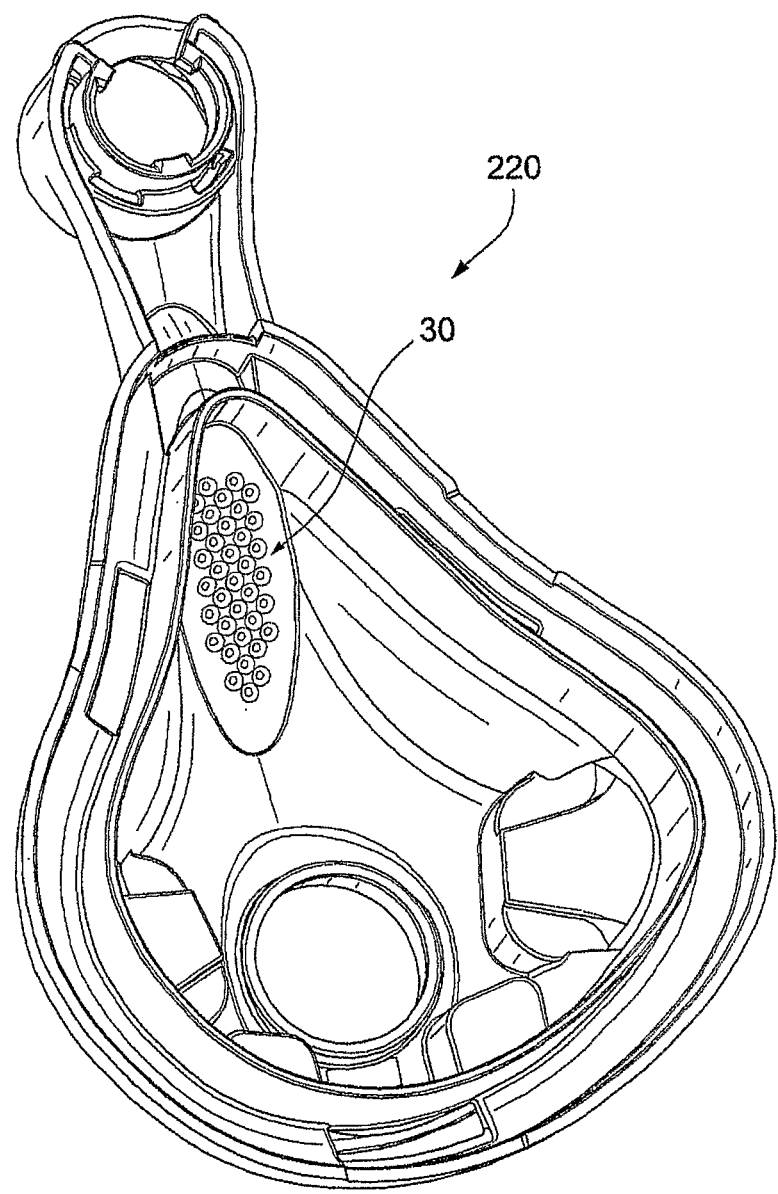
Figure 3:
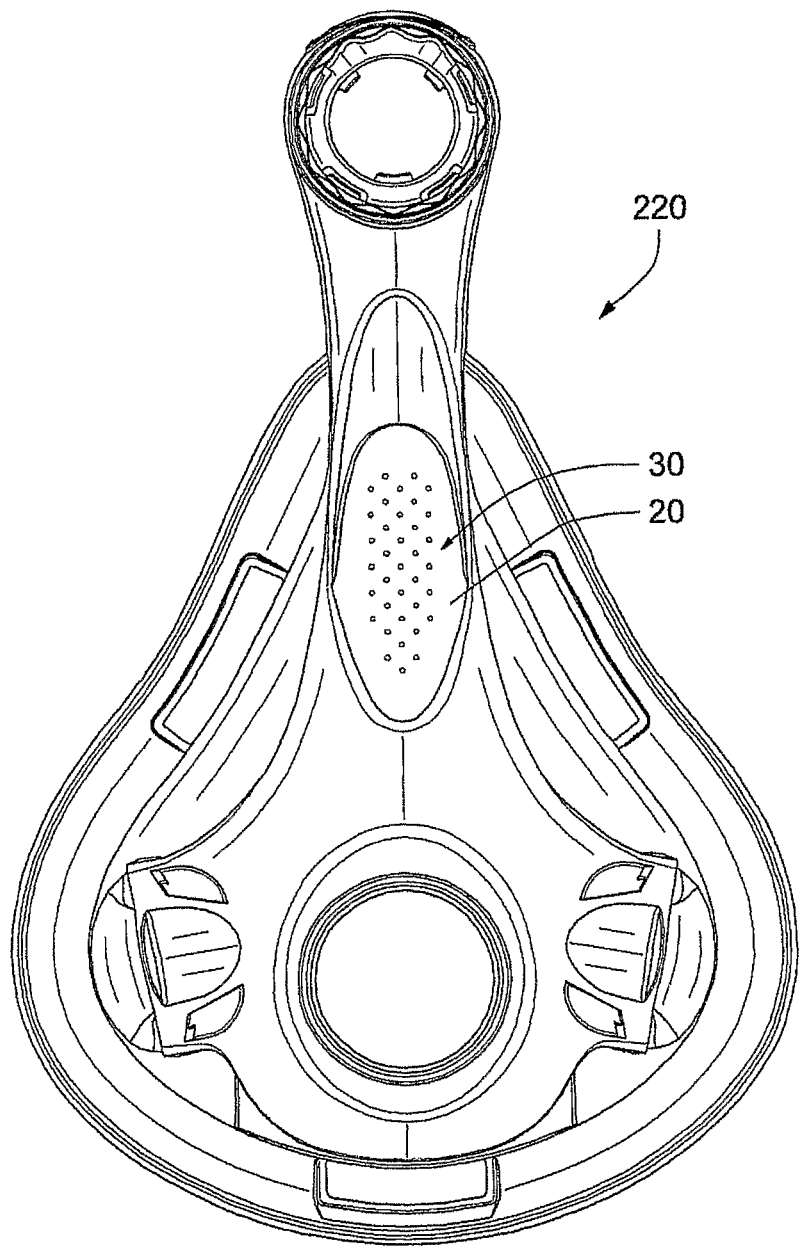
Figures 3, 4:
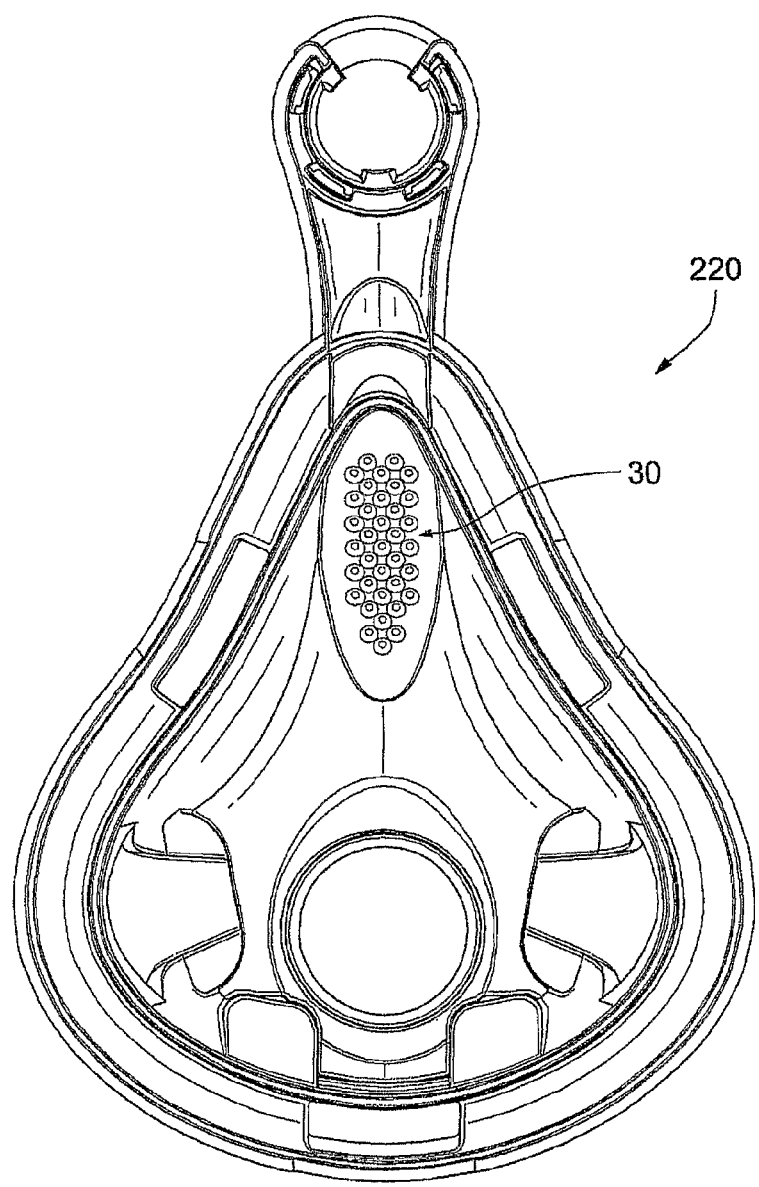
Figures 3, 4, 5:
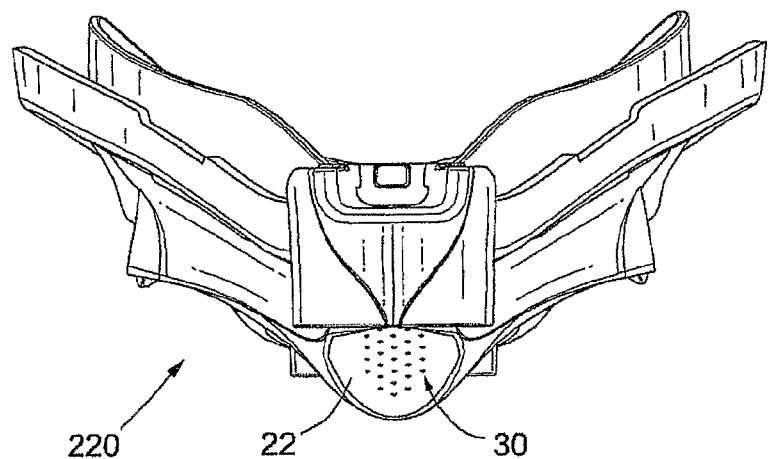
Figures 3, 4, 5, 6:
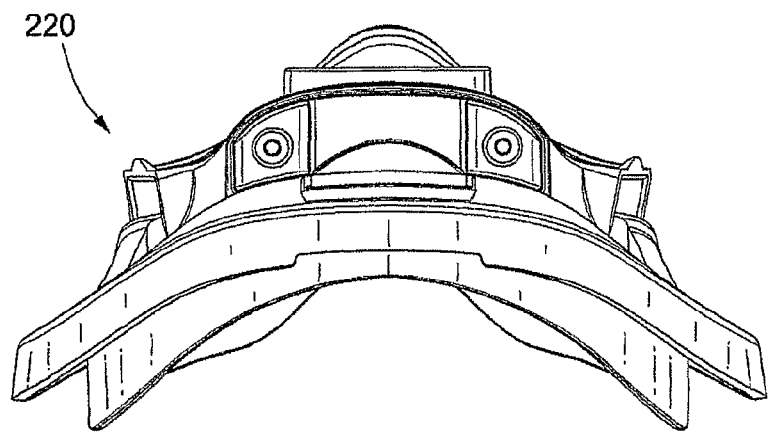
Figures 3, 4, 5, 6, 7:
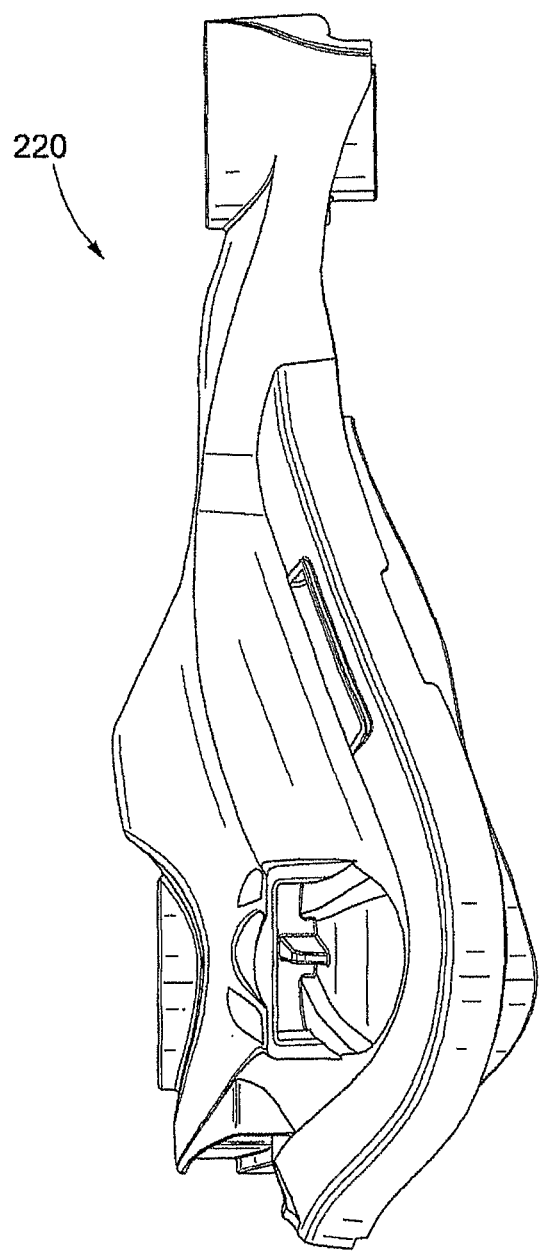
Figures 1, 4:
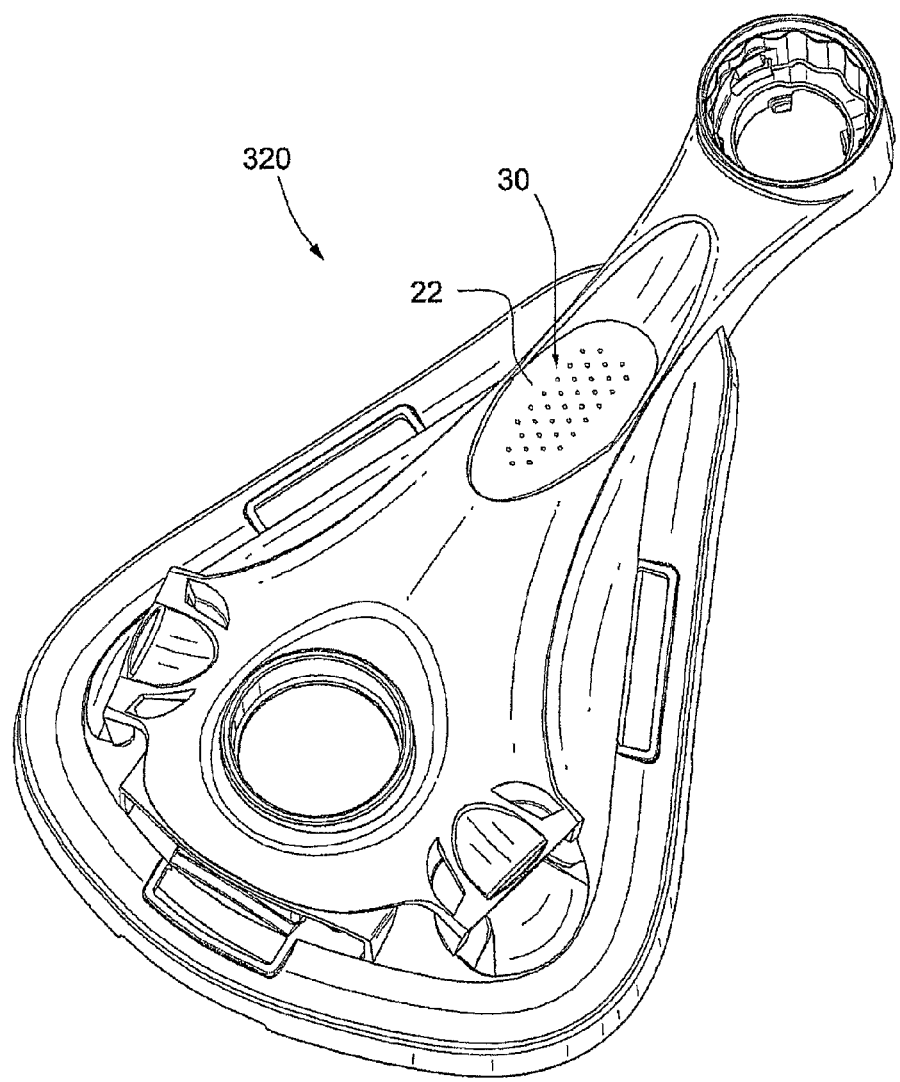
Figures 2, 4:
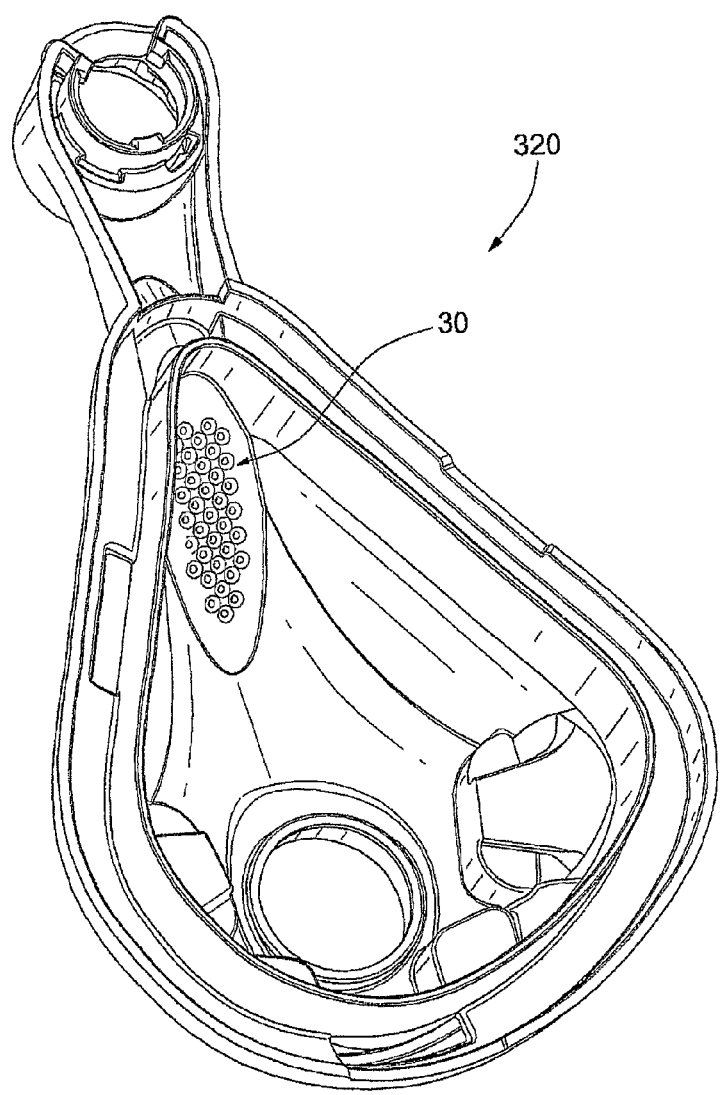
Figures 3, 4:
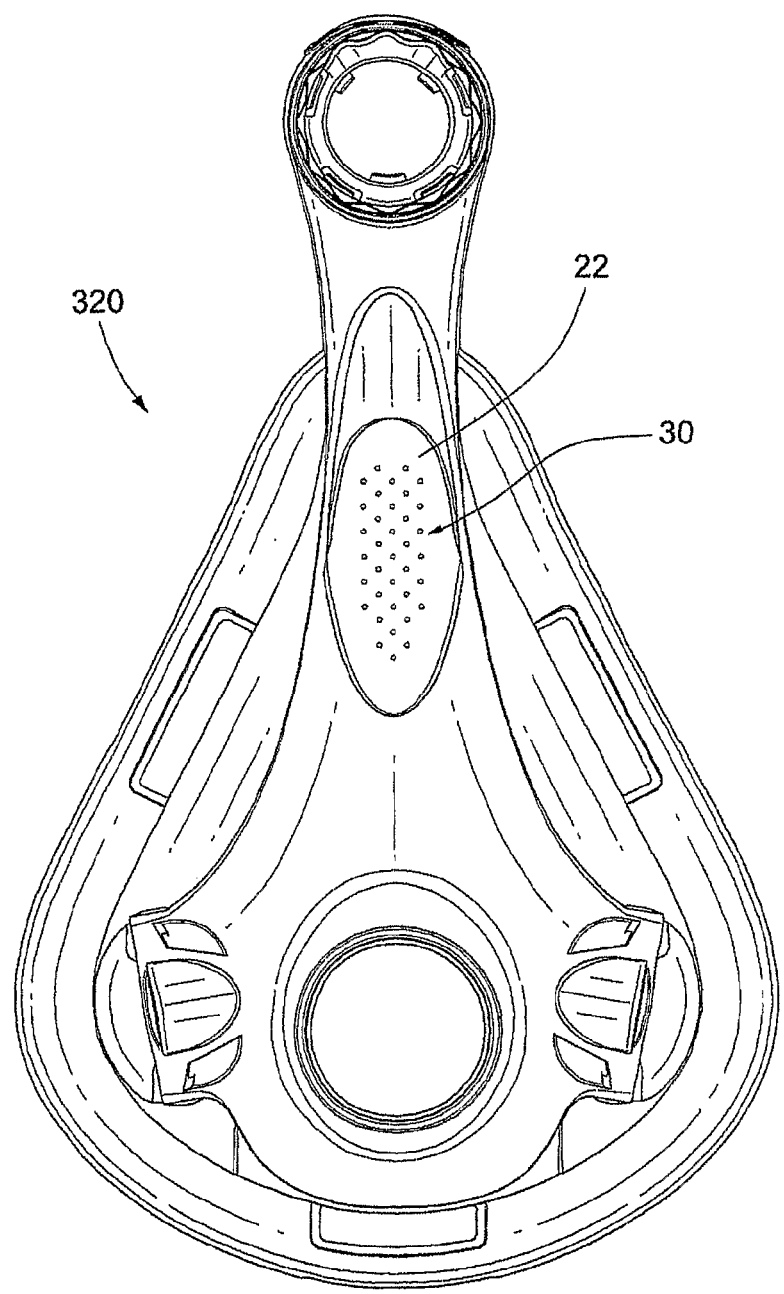
Figure 4:
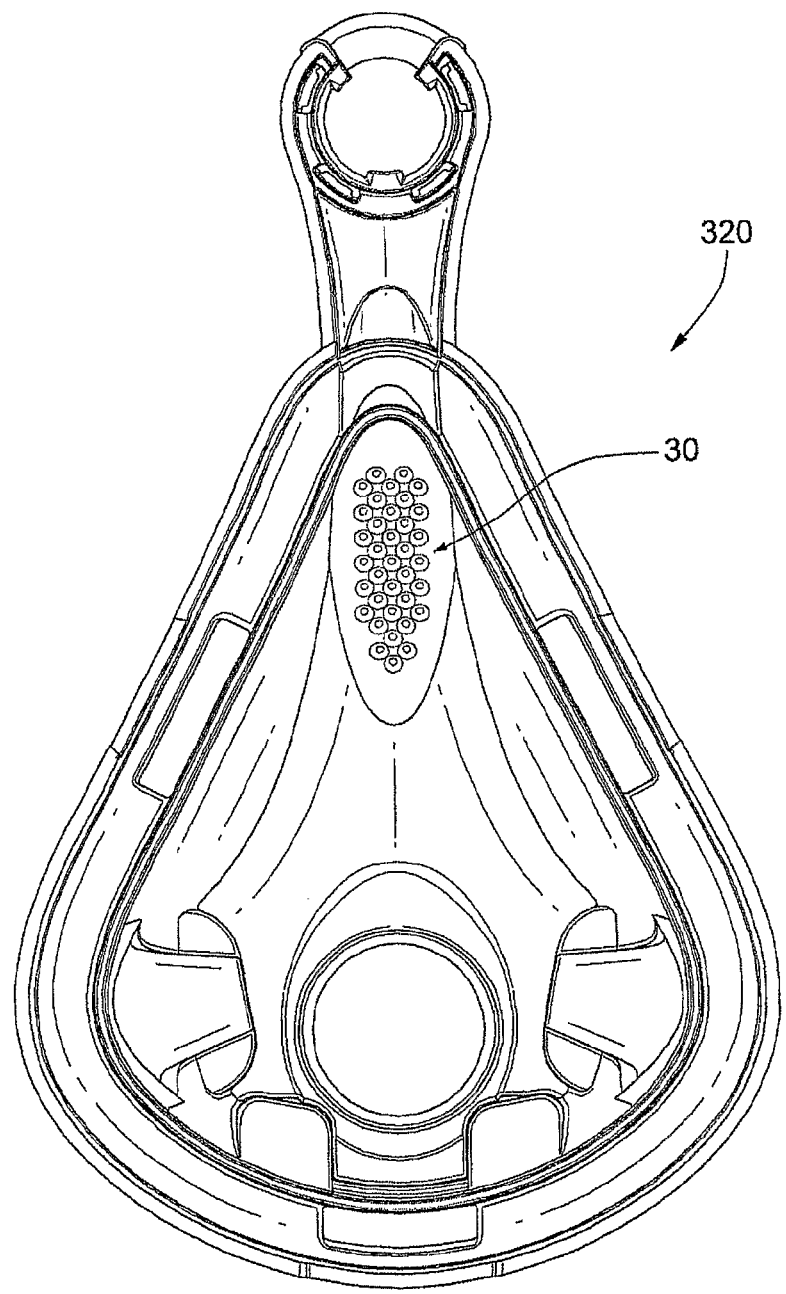
Figures 4, 5:
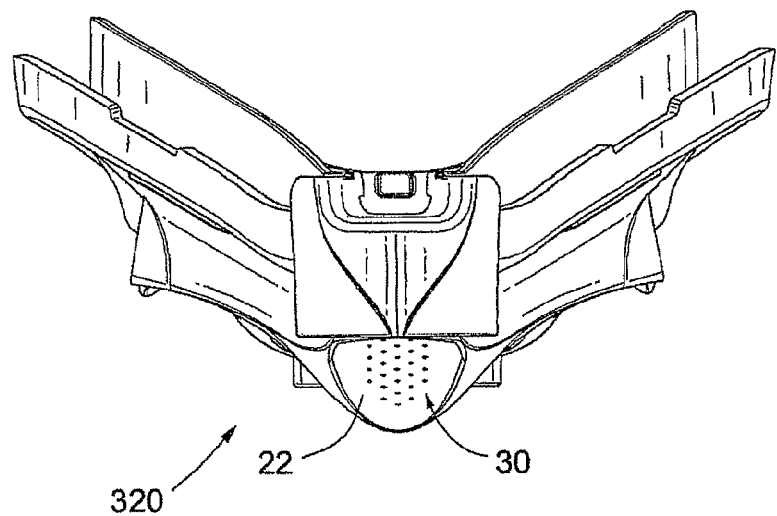
Figures 4, 5, 6:
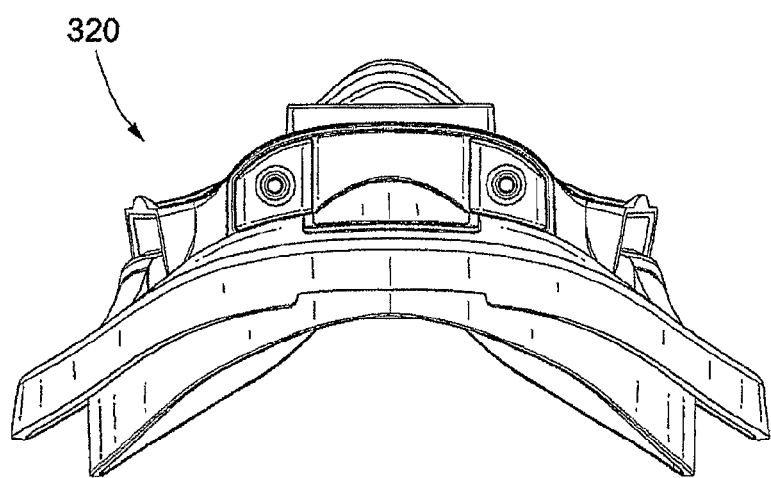
Figures 4, 5, 6, 7:
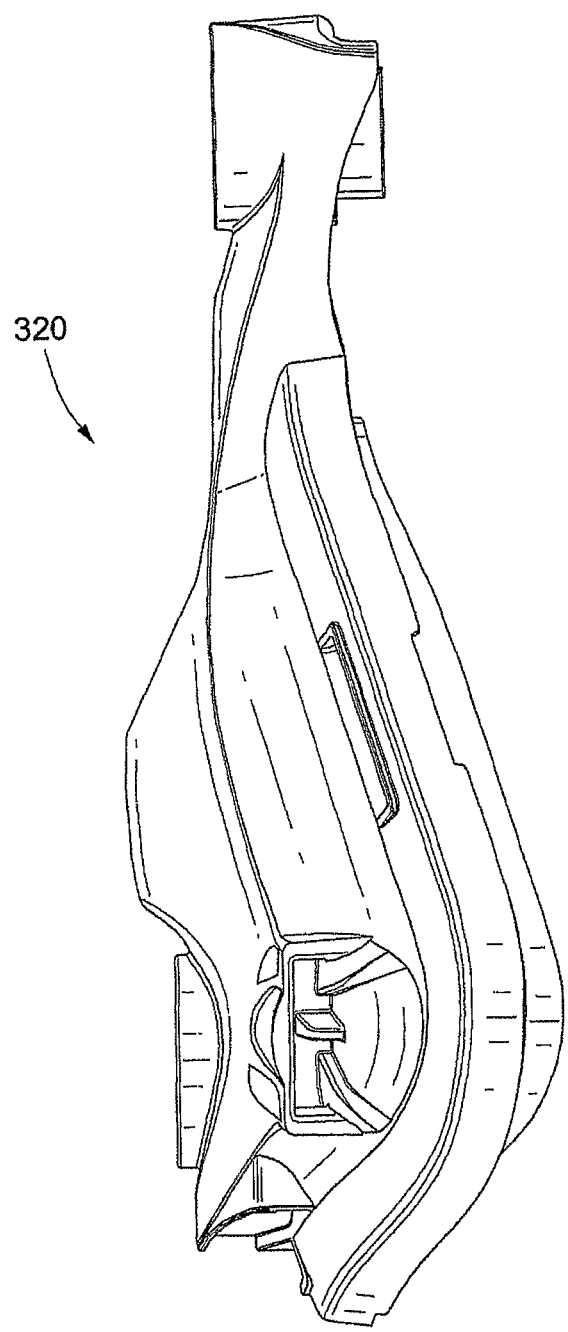
Figures 1, 5:
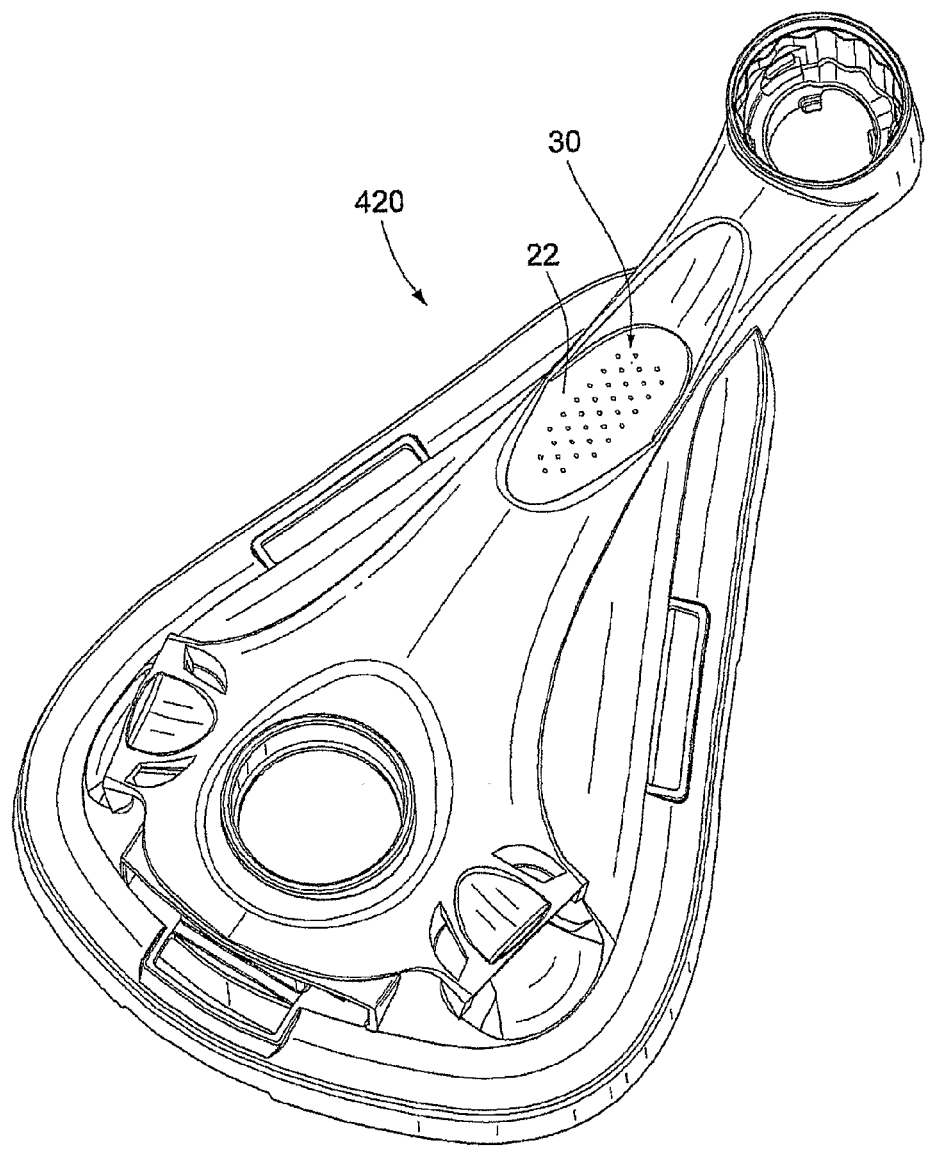
Figures 2, 5:
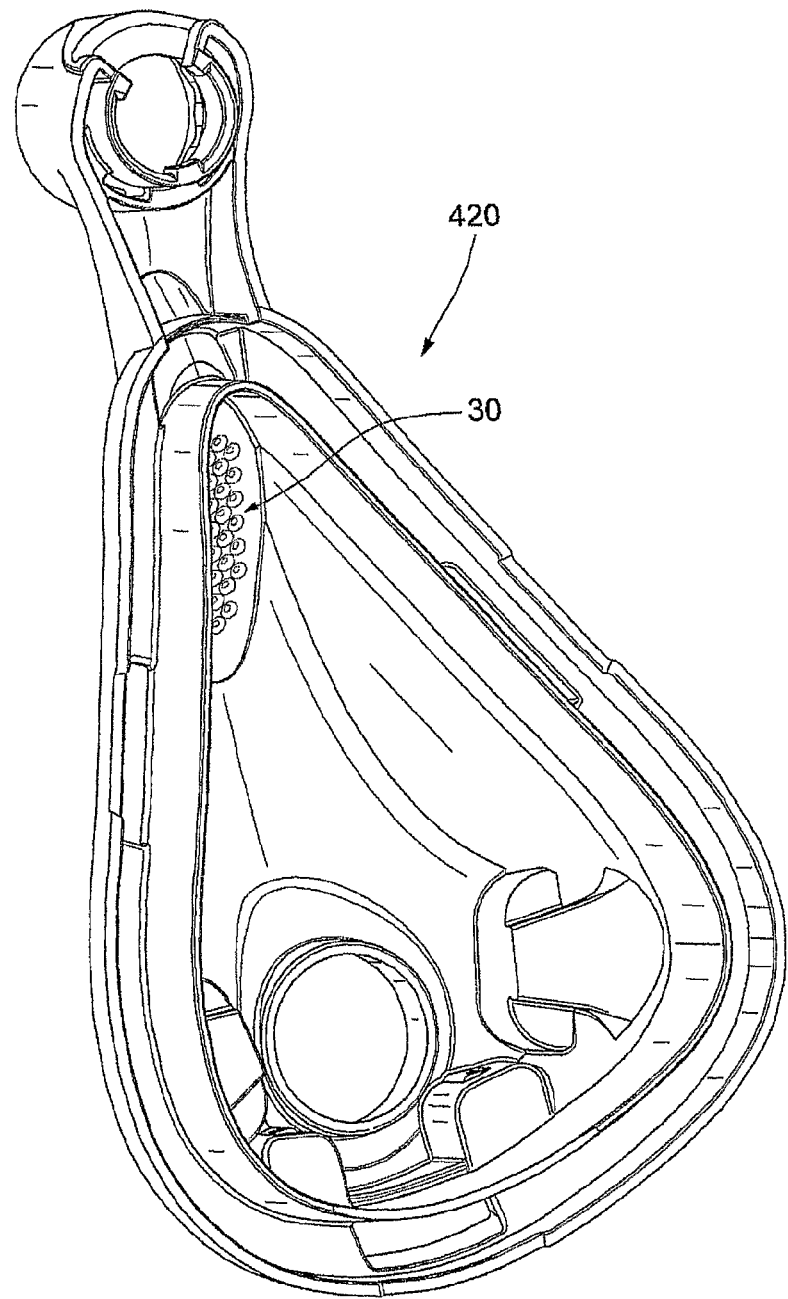
Figures 3, 5:
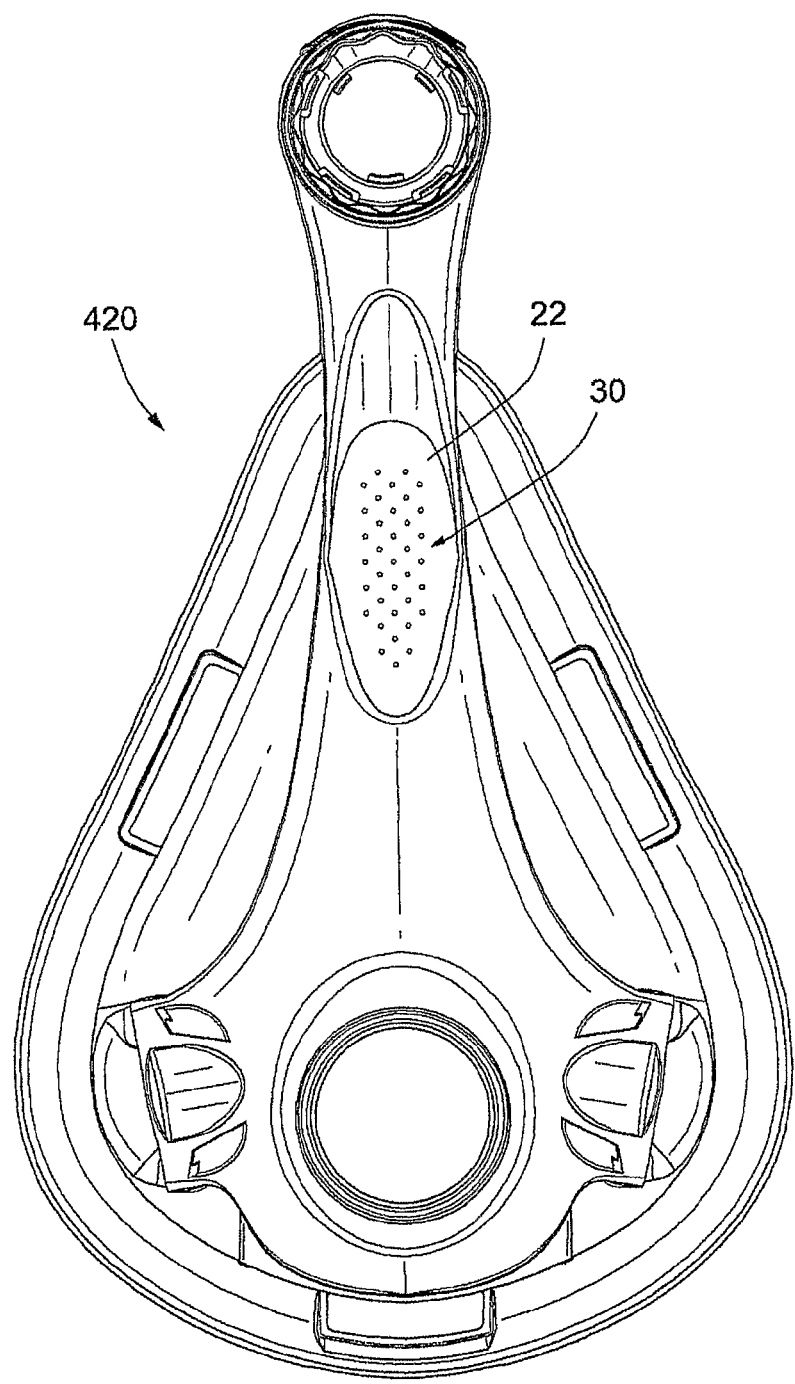
Figures 4, 5:
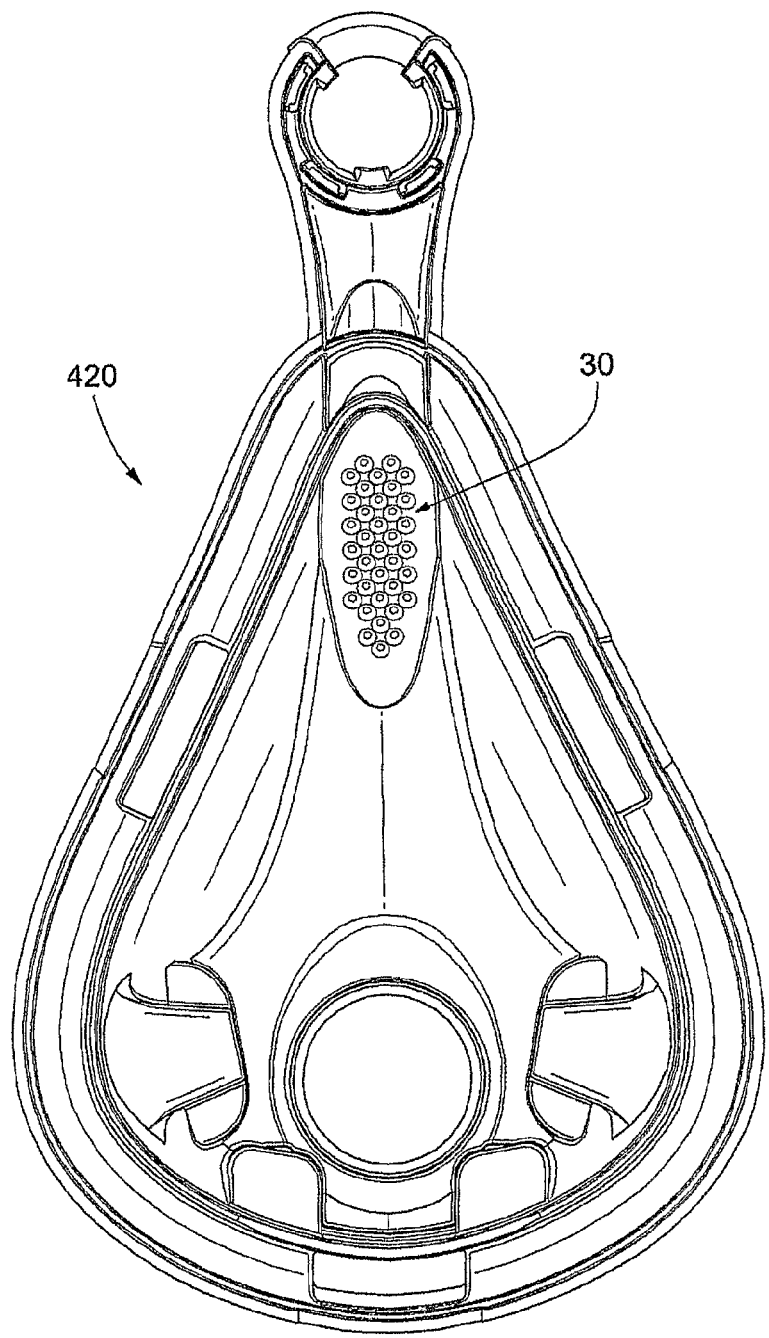
Figure 5:
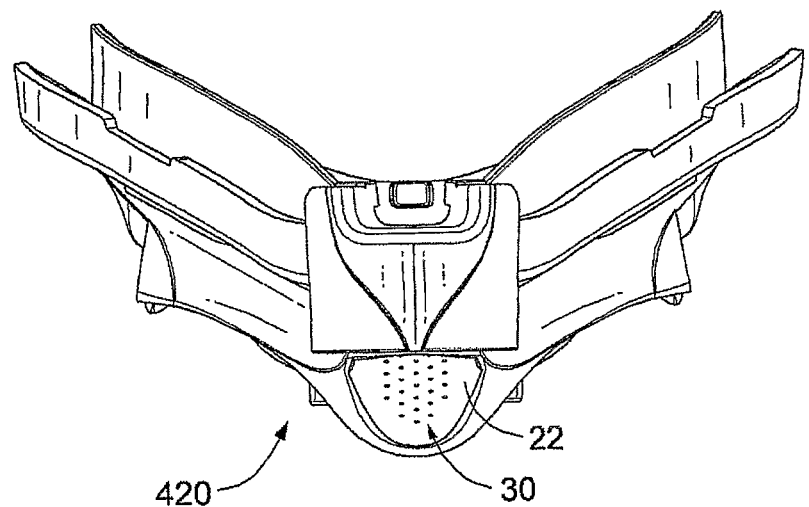
Figures 5, 6:
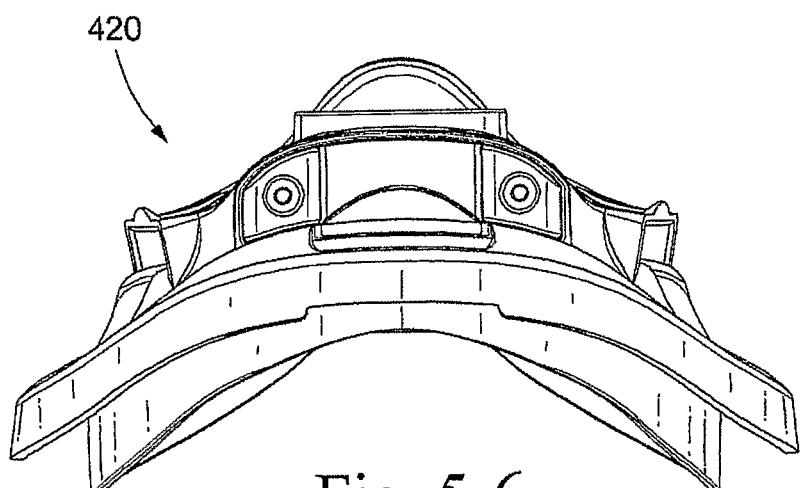
Figures 5, 6, 7:
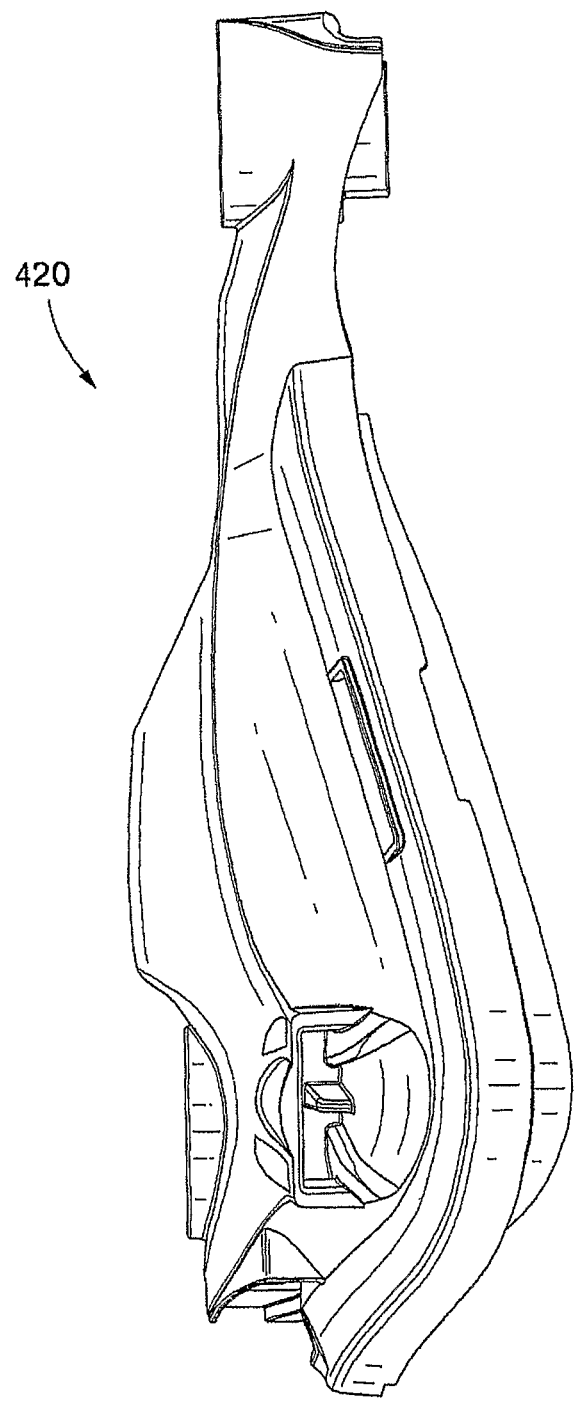

FIG. 1 illustrates an embodiment of a full facial mask assembly ("FMA") 10 including a frame 20 and vent assembly 30 according to an embodiment of the present invention. As illustrated, the mask assembly 10 includes a frame 20, a cushion 40 provided to the frame 20 and adapted to form a seal with the patient's face, an elbow assembly 50 provided to the frame 20 and adapted to be connected to an air delivery tube (not shown) that delivers breathable gas to the patient, and a forehead support 60 to provide a support and stability mechanism between the mask assembly 10 and the patient's forehead. A headgear assembly (not shown) may be removably attached to the frame 20 and the forehead support 60 to maintain the mask assembly 10 in a desired adjusted position on the patient's face.

Further details and embodiments of this type of mask assembly are disclosed in PCT Application Nos. PCT/AU2006/000031, PCT/AU2006/000035, and PCT/AU2006/000037, each of which is incorporated herein by reference in its entirety.

Mask Frame

FIGS. 2-1 to 2-7 illustrate the frame 20 isolated from the other components of the mask assembly 10. As illustrated, the frame 20 includes a main body 65, an upper support member 70 adapted to support the forehead support 60, lower headgear clip receptacles 72 adapted to be engaged with clips 74 (e.g., see FIG. 1) provided to straps of a headgear assembly (not shown), and a lower bore or annular elbow connection seal 76 adapted to engage the elbow assembly 50. Also, the top wall of the frame 20 includes a plurality of slots 78 therethrough, e.g., three slots, that are adapted to engage a cushion clip 80 (portions of clip 80 shown in FIG. 1) that retains the cushion 40 to the frame 20. In addition, the frame 20 includes a vent assembly 30 for gas washout. In an embodiment, the frame 20 is molded in one-piece with polycarbonate.

Vent Assembly

As best shown in FIGS. 2-1 to 2-5, 2-8, and 2-10, the vent assembly 30 is provided to an upper portion of the frame 20. Specifically, the vent assembly 30 is positioned on a relatively flat portion 22 of the frame 20 between spaced-apart side walls 71 of the upper support member 70. As illustrated, the relatively flat portion 22 has a generally oval shape and defines a relatively smooth, planar surface. Moreover, the relatively flat portion 22 is not substantially recessed with respect to the surrounding portions of the frame 20, e.g., not concave.

In an embodiment, as best shown in FIG. 2-10, the relatively flat portion 22 may have a length L of about 40-50 mm, e.g., 44.72 mm, and a width W of about 15-20 mm, e.g., 18 mm. In addition, the relatively flat portion 22 may be inclined with respect to vertical to direct exhausted air upwardly and outwardly from the frame in use. In an embodiment, as best shown in FIG. 2-8, the relatively flat portion 22 may be inclined at an angle α with respect to vertical. The angle α may be about 20°-30°, e.g., 25°. Although specific dimensions and ranges of the relatively flat portion 22 are indicated, it is to be understood that these dimensions and ranges are merely exemplary and other dimensions and ranges are possible depending on application. For example, the exemplary dimensions may vary by 10-20% or more or less depending on application.

This arrangement allows gas to freely exit the vent assembly 30, which results in less noise. Specifically, the vent assembly 30 is positioned on the relatively flat portion 22 so that gas exiting the vent assembly 30 will have less interference with the frame 20. Less gas interference with the frame 20 results in less noise.

In the illustrated embodiment, the vent assembly 30 includes a plurality of holes 35 arranged in a five column pattern. The five column pattern includes a center column 32, flanked by intermediate columns 34, which in turn are flanked by outside columns 36. As illustrated, the columns 32, 34, 36 are aligned or parallel to the longitudinal axis L of the frame 20, e.g., the center column 32 is aligned with the longitudinal axis L and the intermediate and outside columns 34, 36 are parallel to the longitudinal axis L (see FIG. 2-3).

The center column 32 includes 3-20 holes, e.g., 8 holes, the intermediate columns 34 each include 3-20 holes, e.g., 8 holes, and the outside columns 36 each include 3-20 holes, e.g., 6 holes. As illustrated, the holes in the center column 32 are offset with the holes in the intermediate columns 34. Also, the holes in the center column 32 are aligned with the holes in the outside columns 36, with the center column 32 having two additional holes at the lower end.

In the illustrated embodiment, each hole 35 has a generally part conic shape, including opposed walls that converge from a larger (inside) diameter to a smaller (outside) diameter, as viewed in the direction of exhausted gas. In an embodiment, as best shown in FIG. 2-9, D1 may be about 0.65-0.75 mm, e.g., 0.7 mm, D2 may be about 2-3 mm, e.g., 2.4 mm, and D3 may be about 13.5°-14.5°, e.g., 14°. Although specific dimensions and ranges of the hole are indicated, it is to be understood that these dimensions and ranges are merely exemplary and other dimensions and ranges are possible depending on application. For example, the exemplary dimensions may vary by 10-20% or more or less depending on application.

As illustrated, all the holes 35 are positioned within the flat portion 22. The holes are positioned relatively compact such that the holes are nearly touching when viewed from an inner side of the frame (e.g., see FIGS. 2-2 and 2-4). The holes and/or hole arrangement may be designed to reduce noise.

However, the frame 20 may include other suitable vent arrangements. For example, the frame 20 may include vent arrangements such as those described in U.S. Patent Publication No. WO 2006/074516, published Jul. 20, 2006, and PCT Application No. PCT/AU2006/001507, filed Oct. 13, 2006, which claims the benefit of U.S. Design Application No. 29/258,084, filed Apr. 14, 2006, and U.S. Provisional Patent Application Nos. 60/734,282, filed Nov. 8, 2005, 60/758,200, filed Jan. 12, 2006, 60/795,615, filed Apr. 28, 2006, 60/819, 626, filed Jul. 11, 2006, and 60/838,442, filed Aug. 18, 2006, each of which is incorporated herein by reference in its entirety. The vent arrangement is preferably incorporated into the flat portion 22 of the frame 20 so there is less gas interference with the frame 20.

Frame Size

The mask frame 20 may be provided in various sizes, e.g., extra-small, small, medium, and large, to accommodate a wide range of patients. For example, FIGS. 2-1 to 2-7 illustrate an extra-small size frame 20, FIGS. 3-1 to 3-7 illustrate a small size frame 220, FIGS. 4-1 to 4-7 illustrate a medium size frame 320, and FIGS. 5-1 to 5-7 illustrate a large size frame 420. The components of the various size frames 20, 220, 320, 420 are substantially similar and indicated with similar reference numerals. It should be appreciated that any suitable number of sizes may be provided.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask frame for a mask assembly useful for treating sleep disordered breathing of a patient, the frame comprising: a one-piece main body of molded polycarbonate material; and a vent portion adapted to allow washout of gases exhaled by the patient, the vent portion being provided to the main body, the vent portion including a plurality of holes arranged in the polycarbonate material, wherein all of the holes extend through the molded material and are positioned on a continuous, substantially planar portion of the main body, the substantially planar portion containing all of the holes being positioned and aligned between an apex of the main body and an aperture to receive an elbow, the aperture being positioned below the apex, the continuous, substantially planar portion containing all of the holes being centered at the apex, wherein at least a part of the substantially planar portion is not substantially recessed with respect to surrounding portions of the frame, wherein the holes of the vent portion are grouped on the substantially planar portion so that gas exiting the holes will avoid interference with the frame, thereby helping to reduce noise;

wherein the substantially planar portion is positioned on the main body at a location generally corresponding to a nasal bridge of a patient when the mask frame is positioned on a face of the patient;

wherein the main body has a vertical longitudinal axis and the holes are arranged in at least one vertical column aligned with or parallel to the longitudinal axis; and wherein the vent portion includes a pair of intermediate columns parallel to but horizontally offset from the longitudinal axis and a flanking column adjacent to and vertically offset from the respective intermediate column, each said column having at least 6 holes.

2. A mask frame for a mask assembly useful for treating sleep disordered breathing of a patient, the frame comprising: a one-piece main body of molded polycarbonate material; and a vent portion adapted to allow washout of gases exhaled by the patient, the vent portion being provided to the main body, the vent portion including a plurality of holes arranged in the polycarbonate material, wherein all of the holes extend through the molded material and are positioned on a continuous, substantially planar portion of the main body, the substantially planar portion containing all of the holes being positioned and aligned between an apex of the main body and an aperture to receive an elbow, the aperture being positioned below the apex, the continuous, substantially planar portion containing all of the holes being centered at the apex, wherein at least a part of the substantially planar portion is not substantially recessed with respect to surrounding portions of the frame, wherein the holes of the vent portion are grouped on the substantially planar portion so that gas exiting the holes will avoid interference with the frame, thereby helping to reduce noise;

wherein the substantially planar portion is positioned on the main body at a location generally corresponding to a nasal bridge of a patient when the mask frame is positioned on a face of the patient; and wherein the plurality of holes of the vent portion are arranged in a five column pattern.

3. The mask frame according to claim 2, wherein the five column pattern includes a center column, flanked by intermediate columns, which in turn are flanked by outside columns.

4. The mask frame according to claim 3, wherein the center column includes 3-20 holes, the intermediate columns each include 3-20 holes, and the outside columns each include 3-20 holes.

5. The mask frame according to claim 4, wherein the center column includes 8 holes, the intermediate columns each include 8 holes, and the outside columns each include 6 holes.

6. The mask frame according to claim 3, wherein the holes in the center column are offset with the holes in the intermediate columns.

7. The mask frame according to claim 3, wherein the holes in the center column are aligned with the holes in the outside columns.

8. A full-face mask frame for a mask assembly useful for treating sleep disordered breathing of a patient, the mask frame comprising:
a one piece main body comprising polycarbonate, said main body having a lower bore adapted to engage an elbow assembly, said main body defining a longitudinal axis extending though the lower bore and an apex of the main body, said main body having a continuous, substantially planar and smooth vent surface positioned between the lower bore and the apex; and
a pattern of holes adapted to allow washout of gases exhaled by the patient, the pattern of holes being arranged in a plurality of vertical columns, extending substantially parallel to the longitudinal axis, all of said holes and all of said columns being formed within and extending through the polycarbonate and being positioned on the continuous, substantially planar and smooth vent surface, each of said columns having at least 6 holes,
wherein the plurality of columns includes a pair of intermediate columns that are parallel to the longitudinal axis, and an outside column flanking each intermediate column,
wherein the holes in each intermediate column are offset with the holes in the flanking outside column, and
wherein at least a part of the substantially planar and smooth vent surface is not substantially recessed with respect to surrounding portions of the frame.

9. The mask frame according to claim 8, wherein the holes in the outside columns are aligned with each other.

10. The mask frame according to claim 9, wherein the holes in the intermediate columns are aligned with each other.

11. The mask frame according to claim 10, further comprising an upper support member adapted to support a forehead support.

12. The mask frame according to claim 10, wherein a lowermost part of the vent surface is not recessed with respect to surrounding portions of the frame.

13. The mask frame according to claim 12, wherein the vent surface is inclined with respect to vertical so that the holes are adapted to direct exhausted air upwardly and outwardly from the frame.

14. The mask frame according to claim 13, further comprising lower headgear clip attachment points adapted to be engaged with clips provided to straps of a headgear assembly.

15. The mask frame according to claim 14, wherein each hole converges from a larger diameter to a smaller diameter as viewed in the direction of exhausted gas.

16. A full face mask assembly for treatment of obstructive sleep apnea and configured to deliver gas pressurized above atmospheric to a patient, the mask assembly comprising:
the full face mask frame according to claim 15; and
a cushion provided to the mask frame.

17. The mask frame according to claim 8, wherein the vent surface is positioned on the main body so as to reduce noise-inducing interference between gas exiting the holes and adjacent portions of the main body.

18. A mask frame assembly for a mask assembly useful for treating sleep disordered breathing of a patient, comprising:
a one piece main body having a bore extending through polycarbonate material;
an elbow received within the bore; and
a pattern of gas washout vent holes adapted to allow washout of gases exhaled by the patient, the pattern of holes extending through polycarbonate material of the one piece main body, each of said holes being provided on a continuous, substantially planar surface aligned between an apex of the main body and the bore, the bore being positioned below the apex, the continuous, substantially planar surface containing all of the vent holes and being centered at the apex, wherein at least a part of the substantially planar surface is not substantially recessed with respect to surrounding portions of the frame;

wherein the substantially planar surface is positioned at a location on the main body adapted to correspond to a nasal bridge of a patient when the mask frame is positioned on a face of the patient; and wherein at least a portion of the vent holes are arranged in a plurality of columns and the plurality of columns includes five columns each having at least 3-20 holes.

19. The mask frame assembly according to claim 18, wherein said five columns include a center column, an intermediate column on each side of the center column, and an outside column flanking each said intermediate column.

20. A mask assembly for treating sleep disordered breathing of a patient, the mask assembly comprising:
a molded one-piece polycarbonate frame;
a cushion provided to the frame and adapted to form a seal with the patient's face;
an elbow assembly adapted to connect to an air delivery tube to deliver gas to the patient;
a forehead support; and
a headgear assembly adapted to support the frame proximate the user's face,
wherein the frame comprises:
a main body;
an upper support member that supports the forehead support;
lower headgear anchor points adapted to anchor straps of the headgear assembly;
a lower bore that engages the elbow, the lower bore being positioned approximately between the lower headgear anchor points; and
a vent assembly adapted to allow washout of gases exhaled by the patient, the vent assembly being positioned between the lower bore and the upper support member, the vent assembly comprising:
a continuous, substantially smooth planar surface of the frame, the substantially smooth planar surface being inclined such that when the mask assembly is mounted on a patient's face, the substantially smooth planar surface faces upward and away from the patient's face; and
a plurality of holes arranged in a plurality of columns located on the continuous, substantially smooth planar surface, the plurality of columns including intermediate columns flanked by outer columns, the plurality of holes in the intermediate columns being offset from the plurality of holes in adjacent outer columns;
wherein a length of the substantially smooth planar surface in a direction parallel to a vertical longitudinal axis of the frame is longer than a width of the substantially smooth planar surface in a direction perpendicular to the longitudinal axis of the frame,
wherein the intermediate columns are larger than the outer columns, and
wherein at least a part of the substantially smooth planar surface is not substantially recessed with respect to surrounding portions of the frame.

21. The mask assembly according to claim 20, wherein the substantially smooth planar surface is located proximate an apex of the main body.

22. The mask assembly according to claim 21, wherein the substantially smooth planar surface is positioned at a location on the main body adapted to correspond to a nasal bridge of a patient when the frame is positioned on a face of the patient.

23. The mask assembly according to claim 22, wherein the substantially smooth planar surface and the lower bore are oriented in diverging directions.

24. The mask assembly according to claim 20, wherein the substantially smooth planar surface is between spaced-apart side walls that are continuous with spaced-apart side walls of the upper support member.

25. The mask assembly according to claim 20, wherein the holes in the outer columns are aligned with each other.

26. The mask assembly according to claim 25, wherein the holes in the intermediate columns are aligned with each other.

27. The mask assembly according to claim 26, wherein the intermediate columns include a different number of holes than each of the outside columns.

28. The mask assembly according to claim 27, wherein the intermediate column includes more holes than the outer column.

29. The mask assembly according to claim 28, wherein each of the plurality of columns has at least 3-20 holes.

30. The mask assembly according to claim 20, wherein each hole converges from a larger diameter to a smaller diameter as viewed in the direction of exhausted gas.

31. The mask assembly according to claim 20, wherein a lowermost portion of the substantially smooth planar surface is not recessed with respect to surrounding portions of the frame.

32. The mask assembly according to claim 20, wherein the frame is a full face frame.

33. The mask assembly according to claim 20, wherein the holes are oriented and arranged on the frame so as to reduce noise-inducing interferences between gas exiting the holes and adjacent portions of the frame.

34. A mask frame for a mask assembly useful for treating sleep disordered breathing of a patient, the frame comprising:
a one-piece main body of molded polycarbonate material; and a vent portion adapted to allow washout of gases exhaled by the patient, the vent portion being provided to the main body, the vent portion including a plurality of holes arranged in the polycarbonate material, wherein all of the holes extend through the molded material and are positioned on a continuous, substantially planar portion of the main body, the substantially planar portion containing all of the holes being positioned and aligned between an apex of the main body and an aperture to receive an elbow, the aperture being positioned below the apex, the continuous, substantially planar portion containing all of the holes being centered at the apex,
wherein at least a part of the substantially planar portion is not substantially recessed with respect to surrounding portions of the frame,
wherein the holes of the vent portion are grouped on the substantially planar portion so that gas exiting the holes will avoid interference with the frame, thereby helping to reduce noise;
wherein the substantially planar portion is positioned on the main body at a location generally corresponding to a nasal bridge of a patient when the mask frame is positioned on a face of the patient;
wherein the main body has a vertical longitudinal axis and the holes are arranged in at least one vertical column aligned with or parallel to the longitudinal axis; and wherein the at least one vertical column comprises a plurality of vertical columns, the holes of each said vertical column being offset from the holes of an adjacent vertical column.

35. The mask frame according to claim 34, wherein each of said columns includes 3-20 holes.

36. A mask frame for a mask assembly useful for treating sleep disordered breathing of a patient, the mask frame comprising:
   a one piece main body comprising molded polycarbonate material, said main body having a bore adapted to engage an elbow assembly, said main body defining a vertically oriented longitudinal axis extending across a center of the bore, said main body having a continuous vent surface intersecting the longitudinal axis as seen in front view and being positioned superior to the bore, the vent surface being substantially planar as seen in a cross-section taken perpendicular to the longitudinal axis; and
   a pattern of holes adapted to allow washout of gases exhaled by the patient, the pattern of holes being arranged in at least one substantially vertical column positioned on said continuous, substantially planar vent surface, said column extending substantially parallel to the longitudinal axis, all of said holes extending through the molded polycarbonate material and being positioned on the continuous, substantially planar vent surface,
   wherein at least a part of the substantially planar vent surface is not substantially recessed with respect to surrounding portions of the frame,
   wherein the vent surface is positioned and oriented on the main body so as to reduce noise-inducing interference between gas exiting the holes and adjacent portions of the main body,
   wherein the pattern of holes is arranged in a plurality of columns, each of said columns having 3-20 holes, and
   wherein the holes in a first column are offset with the holes in a second column flanking the first column.

37. The mask frame according to claim 36, wherein the first column comprises an intermediate column parallel to and offset from the longitudinal axis, and the second column comprises an outside column flanking the intermediate column.

38. The mask frame according to claim 37, wherein the intermediate column includes more holes than the outside column.

39. A mask frame assembly for a mask assembly useful for treating sleep disordered breathing of a patient, comprising:
   a one piece main body having a bore extending through polycarbonate material;
   an elbow received within the bore; and
   a pattern of gas washout vent holes adapted to allow washout of gases exhaled by the patient, the pattern of holes extending through polycarbonate material of the one piece main body, each of said holes being provided on a continuous, substantially planar surface aligned between an apex of the main body and the bore, the bore being positioned below the apex, the continuous, substantially planar surface containing all of the vent holes and being centered at the apex,
   wherein at least a part of the substantially planar surface is not substantially recessed with respect to surrounding portions of the frame;
   wherein the substantially planar surface is positioned at a location on the main body adapted to correspond to a nasal bridge of a patient when the mask frame is positioned on a face of the patient; and
   wherein the gas washout vent holes are arranged in a plurality of columns, at least two of said columns being vertically offset from one another and each said column having between 3-20 holes.

40. The mask frame assembly according to claim 39, wherein the holes of at least a pair of adjacent columns are offset with respect to one another.

41. The mask frame assembly according to claim 39, wherein the columns include a pair of parallel intermediate columns, and an outside column flanking each intermediate column.

42. The mask frame assembly according to claim 41, wherein the intermediate columns include a different number of holes than each of the outside columns.

43. The mask frame assembly according to claim 42, wherein the holes in the outside columns are aligned with each other.

44. The mask frame assembly according to claim 42, wherein the holes in the intermediate columns are aligned with each other.

45. A mask assembly for treating sleep disordered breathing of a patient, the mask assembly comprising:
   a molded polycarbonate frame;
   a cushion adapted to form a seal with the patient's face;
   a cushion clip that retains the cushion to the frame, the frame including a plurality of recesses to receive the cushion clip;
   an elbow assembly provided to the frame and adapted to connect to an air delivery tube to deliver gas to the patient;
   a forehead support; and
   a headgear assembly adapted to support the mask assembly proximate the user's face,
   wherein the frame comprises:
      a main body;
      a lower bore that engages the elbow; and
      a vent assembly adapted to allow washout of gases exhaled by the patient, the vent assembly being positioned superior to the lower bore, the vent assembly comprising:
         a flat and substantially smooth surface; and
         a plurality of holes arranged through the flat and substantially smooth surface,
   wherein the holes of the vent assembly are not substantially recessed so as to avoid noise-inducing interference between gas exiting from the holes and the adjacent portions of the frame, and
   wherein the plurality of holes is arranged in a plurality of columns, the plurality of columns including intermediate columns flanked by outer columns, the plurality of holes in the intermediate columns being offset from the plurality of holes in adjacent outer columns.

46. The mask assembly according to claim 45, wherein the holes in the outer columns are aligned with each other.

47. The mask assembly according to claim 46, wherein the holes in the intermediate columns are aligned with each other.

48. The mask assembly according to claim 47, wherein each of the plurality of columns has at least 3-20 holes.

49. A mask assembly for treating sleep disordered breathing of a patient, the mask assembly comprising:
   a molded polycarbonate frame;
   a cushion adapted to form a seal with the patient's face;
   a cushion clip that retains the cushion to the frame, the frame including a plurality of recesses to receive the cushion clip;

an elbow assembly provided to the frame and adapted to connect to an air delivery tube to deliver gas to the patient;
a forehead support; and
a headgear assembly adapted to support the mask assembly proximate the user's face,
wherein the frame comprises:
  a main body;
  a lower bore that engages the elbow; and
  a vent assembly adapted to allow washout of gases exhaled by the patient, the vent assembly being positioned superior to the lower bore, the vent assembly comprising:
    a flat and substantially smooth surface; and
    a plurality of holes arranged through the flat and substantially smooth surface,
  wherein the holes of the vent assembly are not substantially recessed so as to avoid noise-inducing interference between gas exiting from the holes and the adjacent portions of the frame, and
  wherein the plurality of holes are arranged in at least four columns, including two intermediate columns and two outermost columns, and wherein a width spanning the outermost columns is less than a diameter of the lower bore.

50. A mask assembly for treating sleep disordered breathing of a patient, the mask assembly comprising:
a molded polycarbonate frame;
a cushion adapted to form a seal with the patient's face;
a cushion clip that retains the cushion to the frame, the frame including a plurality of recesses to receive the cushion clip;
an elbow assembly provided to the frame and adapted to connect to an air delivery tube to deliver gas to the patient;
a forehead support; and
a headgear assembly adapted to support the mask assembly proximate the user's face,
wherein the frame comprises:
  a main body;
  a lower bore that engages the elbow; and
  a vent assembly adapted to allow washout of gases exhaled by the patient, the vent assembly being positioned superior to the lower bore, the vent assembly comprising:
    a flat and substantially smooth surface; and
    a plurality of holes arranged through the flat and substantially smooth surface,
  wherein the holes of the vent assembly are not substantially recessed so as to avoid noise-inducing interference between gas exiting from the holes and the adjacent portions of the frame, and
  wherein the plurality of holes is arranged in at least two substantially vertical columns, the holes in one of the at least two columns being vertically offset from the holes in an adjacent one of the at least two columns.

51. A mask assembly for treating sleep disordered breathing of a patient, the mask assembly comprising:
a molded polycarbonate frame;
a cushion adapted to form a seal with the patient's face;
a cushion clip that retains the cushion to the frame, the frame including a plurality of recesses to receive the cushion clip;
an elbow assembly provided to the frame and adapted to connect to an air delivery tube to deliver gas to the patient;
a forehead support; and
a headgear assembly adapted to support the mask assembly proximate the user's face,
wherein the frame comprises:
  a main body;
  a lower bore that engages the elbow; and
  a vent assembly adapted to allow washout of gases exhaled by the patient, the vent assembly being positioned superior to the lower bore, the vent assembly comprising:
    a flat and substantially smooth surface; and
    a plurality of holes arranged through the flat and substantially smooth surface,
  wherein the holes of the vent assembly are not substantially recessed so as to avoid noise-inducing interference between gas exiting from the holes and the adjacent portions of the frame,
  wherein the plurality of holes is arranged in at least two substantially vertical columns aligned with or parallel to a longitudinal axis of the main body, and
  wherein each of the at least two columns includes at least four holes.

* * * * *

UNITED STATES PATENT AND TRADEMARK OFFICE
CERTIFICATE OF CORRECTION

PATENT NO. : 9,254,370 B2
APPLICATION NO. : 12/312308
DATED : February 9, 2016
INVENTOR(S) : Lynch et al.

Page 1 of 1

It is certified that error appears in the above-identified patent and that said Letters Patent is hereby corrected as shown below:

In the Claims:

In Claim 12, at column 6, line 39, "The mask frame according to claim 10" should be corrected to ---The mask frame according to claim 11---.

Signed and Sealed this
Third Day of May, 2016

Michelle K. Lee
*Director of the United States Patent and Trademark Office*